(12) United States Patent
Shachar et al.

(10) Patent No.: US 8,571,805 B2
(45) Date of Patent: Oct. 29, 2013

(54) METHOD AND APPARATUS FOR DETECTING AND REGULATING VASCULAR ENDOTHELIAL GROWTH FACTOR (VEGF) BY FORMING A HOMEOSTATIC LOOP EMPLOYING A HALF-ANTIBODY BIOSENSOR

(75) Inventors: Yehoshua Shachar, Santa Monica, CA (US); Winston Wu, Alhambra, CA (US); Thomas Chen, La Canada, CA (US); Brett Jordan, Los Angeles, CA (US); Kyle Zimmerman, Los Angeles, CA (US); Herwin Chan, Los Angeles, CA (US); Paladin Luboff, Santa Monica, CA (US)

(73) Assignee: Pharmaco-Kinesis Corporation, Century City, CA (US)

( * ) Notice: Subject to any disclaimer, the term of this patent is extended or adjusted under 35 U.S.C. 154(b) by 788 days.

(21) Appl. No.: 12/820,830

(22) Filed: Jun. 22, 2010

(65) Prior Publication Data
US 2010/0260679 A1    Oct. 14, 2010

Related U.S. Application Data

(63) Continuation-in-part of application No. 12/422,125, filed on Apr. 10, 2009, now Pat. No. 8,145,434.

(51) Int. Cl.
*G01N 33/48* (2006.01)
(52) U.S. Cl.
CPC ..................................... *G01N 33/48* (2013.01)
USPC .......................................................... 702/19
(58) Field of Classification Search
CPC ................................................... G01N 33/48
USPC ................................ 702/19, 22, 23, 182–185
See application file for complete search history.

(56) References Cited

U.S. PATENT DOCUMENTS 6,846,638 B2 *    1/2005    Shipwash ..................... 435/7.1

OTHER PUBLICATIONS

Saerens, "Antibody Fragments as Probe in Biosensor Development," Open Access Sensors, 2008, ISSN 1424-8220.
Yang, "Interdigitated Array Microelectrode-Based Electrochemical Impedance Immunosensor for Detection of *Escherichia coli* 0157:H7," Anal. Chem, 2004,V 76, p. 1107-1113.
Lazcka, "Pathogen Detection: A Perspective of Traditional Methods and Biosensors," Biosensors and Bioelectrics, 2007, vol. 22, p. 1206-1215.
Muller, "VEGF and the Fab Fragment of a Humanized Neutralizing Antibody . . . ," Structure, vol. 6 No. 9, p. 1153-1167, 1998.

(Continued)

*Primary Examiner* — Edward Raymond
(74) *Attorney, Agent, or Firm* — Marcus C. Dawes; Daniel L. Dawes

(57) ABSTRACT

A biosensor for detection of vascular endothelial growth factor (VEGF) hybridization uses an array of parallel capacitors to detect electrochemical binding of circulating VEGF to immobilized anti-VEGF monoclonal half-antibodies (a-VEGF mhAb). Binding of a-VEGF mhAb modulates the threshold voltage of a circuit, changing the impedance of the circuit. An electrode coated with a p-Si substrate enhances the affinity between the VEGF molecules. A fluid cell delivers VEGF samples onto the active surface of the chip. An array of parallel capacitors arranged in an interdigitated pattern detects the VEGF in the fluid. The detector provides an accurately measured and quantifiable rate of change of the VEGF molecules in vivo, providing real time feedback which is used to measure response of the tumor to delivered chemotherapeutic agents and biological response modifiers (BRMs) for the purpose of determining tumor burden and efficacy of the chemotherapy as part of a homeostatic loop for chemotherapy.

28 Claims, 13 Drawing Sheets

(56) References Cited

OTHER PUBLICATIONS

Lee, "Electrical Detection of VEGFs for Cancer Diagnosis . . . ," Biosensors and Bioelectrics, 2009, V 24, p. 1801-1805.

Kang, "Characterization of PEGylated Anti-VEGF Apatmers Using Surface Plasmon Resonance," Macromolecular Research, 2008, V 16 No. 2, p. 182-184.

Hu, "Half-Antibody Functionalized Lipid-Polymer Hybrid Nanoparticles for Targeted Drug Delivery . . . ," Molecular Pharmaceutics, V 7 No. 5, p. 914-920, 2010.

Kim, "Electrochemical Detection of Vascular Endothelial Growth Vactors (VEGFs) Using VEGF Antibody Fragments . . . ," Biosensors and Bioelectrics, 2010, V 25, p. 1717-1722.

\* cited by examiner

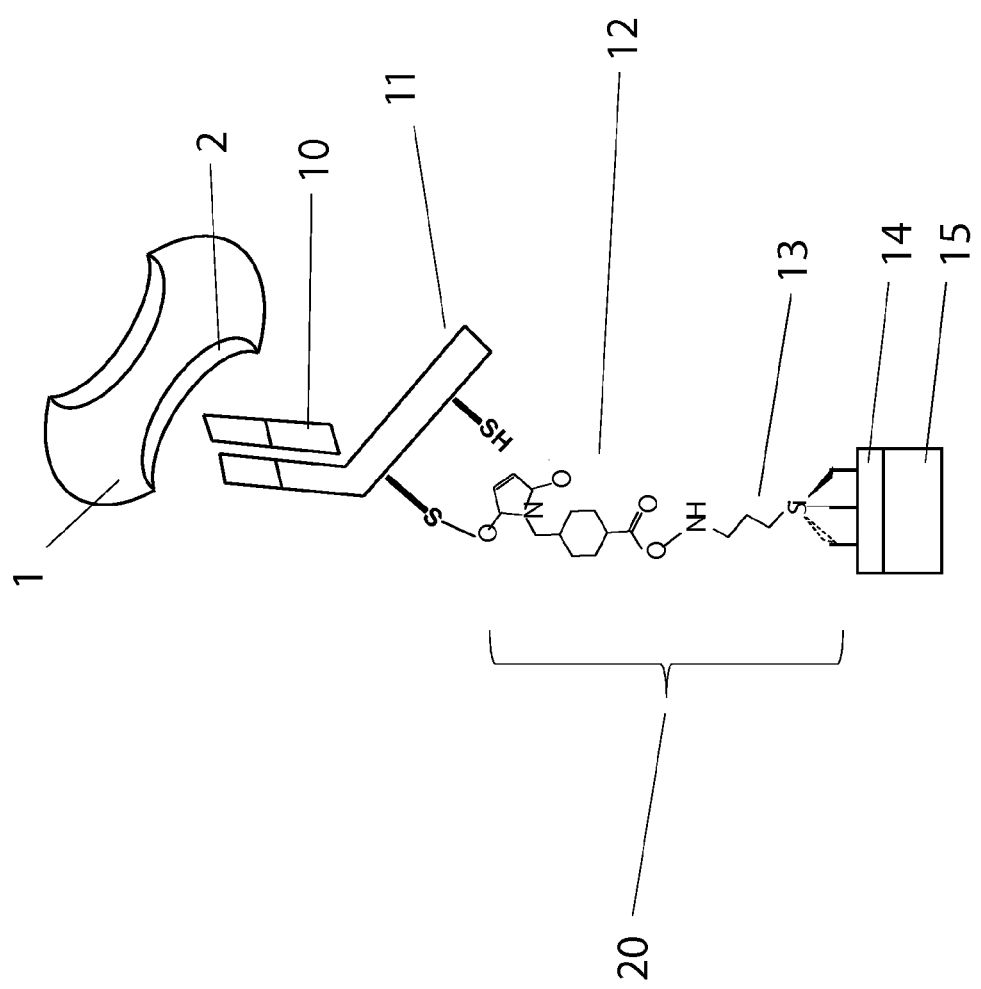

METHOD AND APPARATUS FOR DETECTING AND REGULATING VASCULAR ENDOTHELIAL GROWTH FACTOR (VEGF) BY FORMING A HOMEOSTATIC LOOP EMPLOYING A HALF-ANTIBODY BIOSENSOR

BACKGROUND OF THE INVENTION

1. Field of the Invention

The present invention is directed to chemical biosensors or more particularly to fixed parallel plate chemical biosensors and capacitor arrays and methods of making same utilizing immobilized monoclonal half-antibodies.

2. Description of the Prior Art

In normal physiological development, VEGF is a crucial regulator of vascular development during embryogenesis (vasculogenesis) and blood-vessel formation in the adult (angiogenesis). The members of the VEGF and VEGF-receptor protein families have distinct but overlapping ligand-receptor specificities, cell-type expression, and function. VEGF-receptor activation in turn regulates a network of signaling processes in the body that promote endothelial cell growth, migration, and survival. VEGF also plays a critical role in the pathological angiogenesis that occurs in a number of diseases, including cancer. VEGF and the Flk-1/KDR RTK have been implicated as the key endothelial cell-specific factor signaling pathway required for pathological angiogenesis, including tumor neovascularization. In tumor progression, activation of VEGF pathways promotes tumor vascularization, facilitating tumor growth and metastasis. Abnormal VEGF function is also associated with other diseases including atherosclerosis, psoriasis, age related macular degeneration, diabetic blindness, rheumatoid arthritis, and hyperthyroidism.

Advances in understanding the biology of angiogenesis have led to the development of several therapeutic modalities for the inhibition of the VEGF tyrosine kinase signaling pathway. Inhibition of the VEGF tyrosine kinase signaling pathway blocks new blood vessel formation in growing tumors, leading to stasis or regression of tumor growth. The growth of human tumors and development of metastases depend on the de novo formation of blood vessels to reach and provide nutrients for the hypoxic tumor microenvironment. The formation of new blood vessels is tightly regulated by specific growth factors that target receptor tyrosine kinases (RTKs). Initial attempts to block VEGF by using the humanized monoclonal antibody bevacizumab (Avastin®, Genentech/Roche), and two kinase inhibitors sorafenib (Nexavar; Bayer) and sunitinib (Sutent, Pfizer) targeting the VEGF receptor (VEGF-R) tyrosine kinases are beginning to show promise in human cancer patients, underscoring the importance of optimizing VEGF blockade for neurological cancers. A number of these modalities are under investigation in clinical studies to evaluate their potential to treat various forms of human cancer, but the ability of such studies are limited by the fact that local, real-time in vivo measurement of the VEGF levels and the trends of the VEGF transduction are not readily available.

Biosensors which continuously monitor their surroundings to provide background statistics and warnings against unhealthy conditions are known to be useful in medical technology. In the proposed applications, micro-scale solutions are sought for to minimize cost, minimize impact, and maximize useful lifetime of the biosensor. One-time use biosensors are of limited utility due to the inherent need to monitor the process of the tumor growth and elimination for the duration of treatment.

The prior art discussion on the subject matter of "Biosensors" is extensive and far reaching. There are numerous examples of biosensors (e.g. gravimetric biosensors). The basis of detection is the decrease in the resonant frequency of a resonator that occurs as analyte species attached to the resonating element. Analyte specificity is conferred for biological analytes by functionalizing (treating) the exposed surface of the resonator with ligands that recognize and bind to the target analyte species. Examples of suitable binding entities for target biological analytes include antibodies, receptors, lectins, aptamers and oligonucleotides.

One type of biosensor presented by prior art is the gravimetric biosensor, wherein the immobilized binding group is located in one or more areas on the surface of a membrane. The immobilized binding group locations', size, area, and immobilization density are designed to maximize the observed frequency and/or amplitude shifts on the membrane by the target analyte binding. This, in turn, maximizes the discrimination observable by subsequent frequency and/or amplitude shifts on the membrane based upon all combinations of specific and non-specific binding. This discrimination may take three forms: (a) change in resonant frequency of the membrane, (b) appearance or disappearance of higher order harmonic vibrations, or (c) change in amplitude decay rates. In such a biosensor, a single membrane may be comprised of a plurality of individually addressable elements for actuation and for sensing purposes. That permits the specific excitement of selected higher order vibrational modes and enables simultaneous vibration actuation of an alarm circuit or like devices. The principles of acoustic wave analysis, which can be utilized in a gravimetric sensor, is well known and has appeared in literature for more than a decade.

Molecular interactions can be detected electronically through the polarizability of biological macromolecules, optically through the use of fluorescencing tags, radiometrically through the use of radioactive labeled tags, or acoustically. Recently, MEMS based sensors have been incorporated in the biotechnical and biomedical fields. Application of acoustic biosensors include cell detection, glucose biosensing, antibody-antigen recognition, and protein adsorption detection.

Piezoelectric quartz crystal microbalances (QCMs) have been used since the late 1950s to detect gas and liquid phase analytes. Application of QCM technology to biological analytes is more recent. QCMs have been used to track the non-specific adsorption of proteins to unmodified and modified quartz crystal surface electrodes. Immobilization of antibodies to the crystal surface confers analyte specificity.

What is needed, is an apparatus that allows an architecture for constructing a solid-state biosensor for label-free detection of VEGF hybridization.

SUMMARY OF THE INVENTION

The following summary of the illustrated embodiments of the invention is provided to facilitate an understanding of some of the innovative features unique to the present invention and is not intended to be a full description. A full appreciation of the various aspects of the invention can be gained by taking the entire specification, claims, drawings, and abstract as a whole. Additional objects and advantages of the current invention will become apparent to one of ordinary skill in the art upon reading the specification The of the illustrated embodiments of the invention is directed to biosensors built by an integrated platform using solid state fabrication techniques in conjunction with protein elements known as humanized monoclonal antibodies that are selected for high-affinity binding to specific protein targets. Specifically, the hybridization between VEGF molecules found in tumor fluid withdrawn from metastasized regions and immobilized a-VEGF mhAb changes the electrochemical properties of sensor electrodes that can be detected by the electrical circuit of the apparatus. The illustrated embodiments of invention aim to correlate the growth rate of tumor development with VEGF level in the tumor fluid by measuring the binding rate of VEGF molecules to the capacitor plate, and project the progress of the chemotherapy with vector/trends of the VEGF sensing. The capacitor plates are arranged in an interdigitated pattern to maximize the detection surface area in a given sensor volume.

An implanted in vivo device that accurately provides real time feedback on VEGF levels is crucial for any finely tuned anti-angiogenesis therapy, enabling a system to be logically regulated, and attenuate or modify the intake of anti-angiogenic agents. The illustrated embodiments of invention measure VEGF levels by emulating the process whereby VEGF binds to an anti-VEGF monoclonal antibody within a known time domain, and provides appropriate VEGF level feedback for use in a regulated drug and chemotherapy feedback loop.

Fabrication of the proposed VEGF detector is presented, using the significant improvements made in techniques and equipment for fabricating miniature devices and, consequently, the use of micro machined equipment is outlined. Improvements in silicon manufacturing and high-precision machinery opened the area now known as micro-electromechanical systems (MEMS) for research and development of applications. Subsequent development of microscale valves, pumps, channels and heat exchangers allowed for manipulation of extremely small fluid volumes. Coupled with mass fabrication techniques refined in the integrated circuit (IC) and MEMS communities, microfluidic and microchemical systems are employed in realizing the illustrated embodiments of the invention.

The illustrated embodiments of the invention include a coordinated and flexible sensor system with multiple devices operating on a single fluid sample. The device is capable of carrying out fully automated chemical analysis with the aid of on-board processing logic.

The illustrated embodiment includes an apparatus that allows an architecture for constructing a solid-state biosensor for label-free detection of VEGF hybridization. Such a device is realized by forming a matrix array of parallel capacitors arranged in interdigitated pattern, so as to achieve a high ratio signal to the lowest minimal electrochemical variations, accompanied by an electrical equivalent value, thus allowing the realization of low-cost, portable, fully integrated devices.

Biosensors for detecting the presence of molecules of interest have application in numerous fields, including medical diagnosis, biomedical research, and detection of agents used in biological and chemical warfare. The need exists for an inexpensive, compact sensor with high sensitivity for detecting VEGF molecules in a real-time, in vivo, and label-free environment to report on the conditions such as trends of concentration levels, further enabling the formation of a closed feedback loop to effectively regulate, (attenuate, modify), the biological activity using medications.

In general, biological target complexes are tagged by a seed substance that can catalyze the formation of a surface-enhanced substrate such as monoclonal antibody. The target complexes can then bind to capture reagents which include a VEGF label. The substrate is then generated on the seed substance through reduction of immobilized capture molecules such anti-VEGF monoclonal half-antibody (a-VEGF mhAb).

Accordingly, in one embodiment, a biological target complex including a target analyte associated with a first specific binding member is provided. The target complex further includes a second specific binding member that binds to the first specific binding member forming a target complex. The second specific binding member includes a seed particle suitable for catalyzing the formation of a surface enhanced a-VEGF mhAb substrate. In another embodiment, any seed particles suitable for binding to any of the known cancer markers can be attached to the target complex using the method disclosed. Subsequently, the complex substrate can be activated by means of the electronic circuit to provide the necessary change in impedance effect. These and other important objects will be apparent from the descriptions of the instant invention which follow.

It is object of one embodiment of the invention to propose a fluid-cell configured so as to enable the flow of VEGF samples on the active surface of the chip. The rate of fluid flow through the sensor is controlled so that both hybridization and de-hybridization of VEGF molecules in the fluid to the immobilized a-VEGF mhAb can be achieved. A detailed calculation of the hybridization energy presented as part of a plan to de-hybridize and wash away the VEGF molecules so that the sensor is re-useable further detection.

The apparatus is further required to detect the presence of the VEGF molecules by the use of mechanism based on an electrochemical binding of a monoclonal antibody suitable to bind to VEGF. When the blood or tumor fluid flows through the biosensor, the floating VEGF antigen will be captured by the surface immobilized anti-VEGF half-antibody, in which the antigen binding site (called Fab) of the half-antibody specifically binds to the epitope site of the antigen. The binding is driven and determined by a combination of the following forces: electrostatic bond, hydrogen bond, Van del Waals force, hydrophobic force, and aromatic pi bond.

In a specific further development, the method of at least one embodiment of the invention advantageously makes use of the methodology of electrochemical detection, especially of redox cycling in combination with a monoclonal antibody label to produce half-antibodies. The disulfide bonds connecting the two heavy chains of a-VEGF mAb are selectively cleaved to produce two a-VEGF mhAb, which possess intact binding sites and reactive thiol groups and can be conjugated in a site-specific manner to bind to VEGF.

An objective of producing two half antibodies out of a single VEGF mAb is reduce the binding affinity level between Fab of the immobilized a-VEGF mhAb and the VEGF. This binding affinity level is less than the reported VEGF to a-VEGF mAb bond (Kd=3.4±0.9 nM).

It is a further object of the invention to utilize a-VEGF mhAb half antibody molecule because the binding affinity of a-VEGF mhAb and VEGF is lower than the binding affinity of all other bonds generated in the creation of the biosensor surface. Because the affinity of the bond between aVEGF mhAb and VEGF has high specificity but weaker affinity than other bonds presented in this invention, the VEGF molecules may be 'released' from their bond to aVEGF mhAb molecules, allowing the biosensor surface to be re-used multiple times. This 'release' is generated by the introduction of a small electric current on the biosensor plates to provide an energy source, as well as by a flow of fluid generated by the piezoelectric micro-fluidic pumps disclosed within this invention.

Another development is the preparation of the silicon surface with maleimide-terminated self-assembly monolayers (SAMs) so that the a-VEGF mhAb can directly bind to the surface and are immobilized in orientation-specific manner to the SiO2 surface. This chemical reaction will keep the antigen-binding site of a-VEGF mhAb toward outside. The coating density of the a-VEGF mhAb on the substrate will be determined by the concentration of hAb during the preparation.

An object of one embodiment of the invention is to produce a sensor shall possess an electrical polarity so as to naturally attract the intrinsically negative electric charge of VEGF molecules, while further modulating the threshold voltage of the circuit. The novel sensor shall be constructed with an insulated electrode preferably coated with a p-Si substrate so as to help bring down the VEGF molecules to the surface of the electrodes, and enhance the affinity between the VEGF molecules and the antibody. Another object of the invention is to be able to reverse the electrical polarity so as to expel and release the VEGF from the immobilized a-VEGF mhAb. The force generated by the electrical polarity is such that it can overcome the VEGF to a-VEGF mhAb binding due to electrostatic bond, hydrogen bond, Van del Waals force, hydrophobic force, and aromatic pi bond, but less than the covalent bonds between the various linker molecules.

Another object of one of the embodiments of the invention is a device shall have an array of parallel electrodes arranged in an interdigitated pattern to maximize the surface area for VEGF hybridization and improve the detection sensitivity.

The various embodiments of the invention relate to signal amplification methods for multiple biological assays with at least one device for monitoring the hybridization of the VEGF molecules over the matrix array positions of the chip. The device shall be equipped with a computational apparatus so as to render the sensory output over the time domain, resulting in detection, reporting and formation of a homeostatic loop to guide therapeutic intervention of a medicating agent(s). The apparatus periodically measures, stores, and reports the electrical values of sensory output pertaining to the hybridization of the VEGF molecules to the immobilized a-VEGF mhAb.

One embodiment of this invention is the in vivo detection of VEGF molecules not only provides information on the current state of tumor burden but its trend over time can be used to project efficacy of chemotherapeutic agents and biological response modifiers (BRMs) for the purpose of tumor burden reduction and elimination.

One object of an embodiment of the invention is the real-time monitoring via a wireless radio of the VEGF detection sensory output pertaining to information on the current state of tumor burden. The apparatus shall be equipped with a medical implant communication service (MICS) wireless radio approved for transcutaneous radio frequency (RF) communication.

Another embodiment of the invention is to control the hybridization of the VEGF molecules over the matrix array positions of the chip with a pump. There is at least one device for controlling the rate of liquid flow and associated control devices are present on the arrangement of at least one embodiment of the invention. For this specific purpose, the sensor chip is connected to a microfluidics system including precision pump in at least one embodiment. One specific capability of the liquid flow control is to allow for flushing away the de-hybridized VEGF molecules from the electrodes after detection is complete, enabling the sensor to be reused repeatedly.

BRIEF DESCRIPTION OF DRAWINGS

The accompanying figures, in which like reference numerals refer to identical or functionally-similar elements throughout the separate views and which are incorporated in and form part of the specification, further illustrate the present invention and together with the detailed description of the invention, serve to explain the principles of the present invention.

FIG. 3 is a graphic depiction of the VEGF sensor with its constituent hybridization elements.

DEFINITIONS

Figure 1:
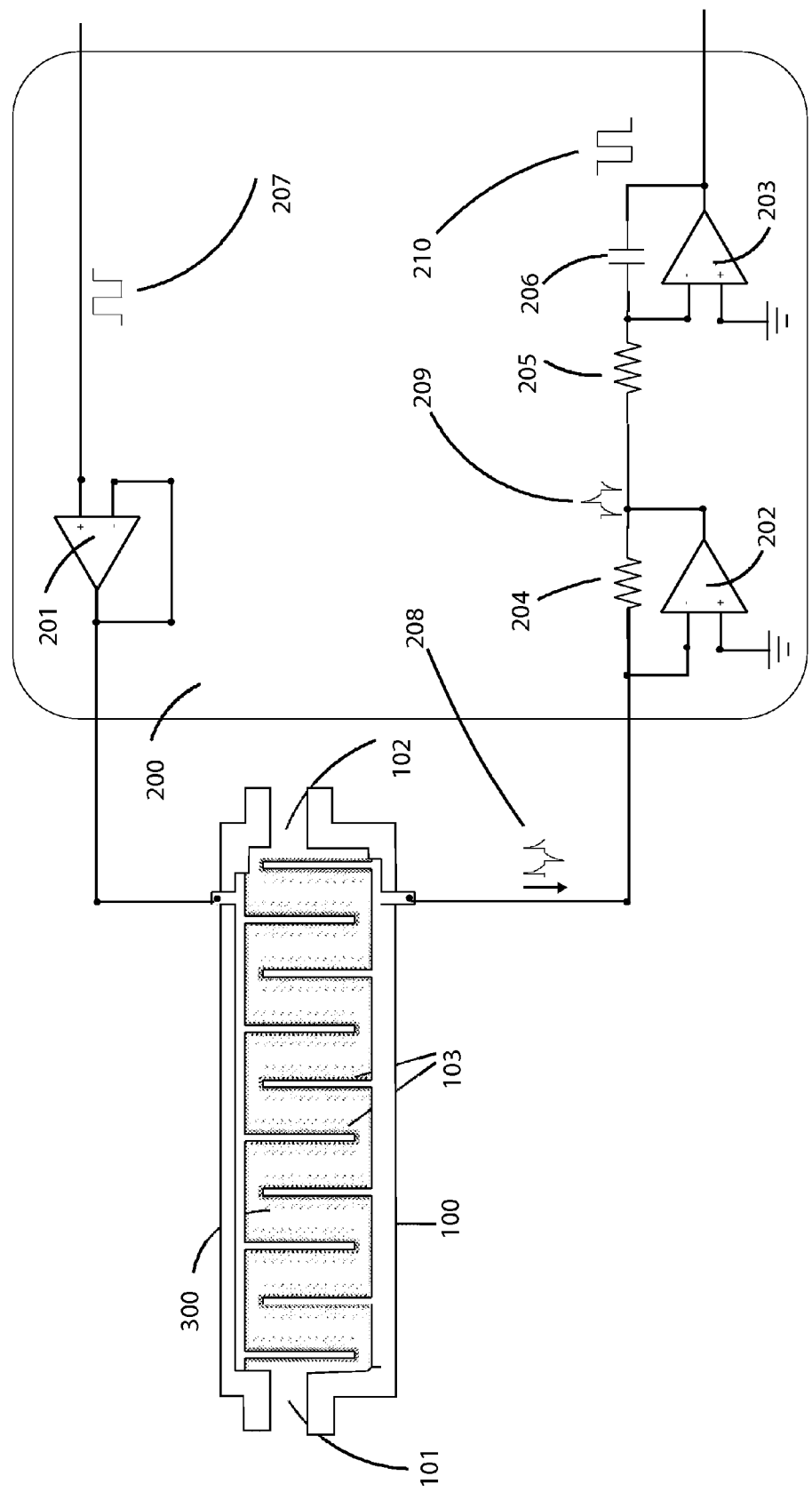
FIG. 1 is an orthographic cross sectional view of the apparatus with a schematic representation of the electronic detection module.

All technical, scientific or other terms used herein have the same meanings as commonly understood by one of ordinary skill in the art to which this invention pertains. The definitions provided below are intended to clarify or illustrate the ordinary meaning of the defined terms and are not to be construed as limiting or narrowing the scope of meaning of those terms. Although any methods and materials similar or equivalent to those described herein can be used in the practice or testing of the present invention, the methods, devices, and materials are now described. All publications mentioned herein are incorporated herein by reference for the purpose of describing and disclosing the materials and methodologies which are reported in the publications which might be used in connection with the invention. Nothing herein is to be construed as an admission that the invention is not entitled to antedate such disclosure by virtue of prior invention.

"Humanized Anti-VEGF Monoclonal Half-Antibody" as used herein refers to the resulting two monoclonal antibody fragments after the disulfide bonds connecting the two heavy chains are cleaved by Tris(2-carboxyethyl) phosphine (TCEP). The resulting half-antibodies (hAb) possess intact binding sites and reactive thiol groups. These hAb retain their targeting ability but are smaller in size and can be conjugated in a site-specific manner as well as to react with the maleimide-terminated SiO2 surface.

"VEGF-A and Anti-VEGF Monoclonal Antibody Hybridization" as used herein refers to the process of hybridization of VEGF 1, to the anti-VEGF monoclonal antibody 11, and is accomplished via the molecular recognition between VEGF-A and the anti-VEGF monoclonal half-antibody. The humanized anti-VEGF monoclonal antibody (rhuMab VEGF; bevacizumab; Avastin®) bound VEGF with affinity very similar to that of the original antibody (Kd~0.5 nM). In common with its mouse counterpart, bevacizumab binds to and neutralizes all human VEGF-A isoforms and bioactive proteolytic fragments. The binding epitope of bevacizumab has been defined by crystal structure analysis of a Fab-ligand complex. This analysis predicts that Gly88 in human VEGF is essential for binding bevacizumab and this residue also underlies the species specificity of bevacizumab binding, since a serine residue is found in mouse and rat VEGF at the corresponding position. Bevacizumab does not neutralize other members of the VEGF gene family, such as VEGF-B or VEGF-C. The pharmacokinetic properties of bevacizumab in several species have been previously described and are consistent with a typical humanized monoclonal antibody. The terminal half-life of bevacizumab in humans is 17-21 days. Importantly, no evidence of antibody response to bevacizumab has been found in any clinical trials so far performed, verifying the success of the humanization.

"Anti-VEGF Monoclonal Half-Antibody Immobilization" as used herein refers to the process of binding the half antibody to the surface, in which Maleimide-thiol coupling occurs rapidly and spontaneously. The maleimide-terminated SiO2 substrate will be incubated with anti-VEGF hAb solution at a desirable concentration for 2 hrs. The hAb will spontaneously couple to the substrate surface in an orientation-specific manner. As illustrated in FIG. 3, the antigen-binding site will be kept toward outside. The concentration of the anti-VEGF hAb will be used to control the hAb coating density on the substrate. After incubation, the substrate will be rinsed with PBS buffer to remove all unconjugated compounds.

"Characterization of the Anti-VEGF Half-Antibody Immobilization" as used herein refers to the process of confirming and quantifying the coupling reaction by using fluorescence measurements. Before TCEP reduction, anti-CEA mAb will be covalently labeled with Alex-488 fluorophores. To confirm that the retained fluorescence is due to maleimide-thiol conjugation rather than non-specific absorption of anti-VEGF hAb or uncleaved mAb, intact mAb will be used as a negative control to ensure that mAB will not absorb and stick to the substrate after rinsing with PBS buffer. Next, VEGF proteins will be used to further evaluate the binding sensitivity and specificity of the immobilized anti-VEGF hAb.

"Surface Modification" as used herein refers to the process of preparing the SiO2 surface 14, as it is first treated with piranha solution (H2SO4:H2O2=3:1 (v/v)) for 20 mins, followed by rinsing with distilled water, to completely clean the surface. Next, the substrate will be soaked in 50% ethanol solution (EtOH:H2O=50:50 (v/v)) for 2 hrs to fully hydrate the surface. Then the hydrated surface will be treated with piranha solution for additional 20 mins and washed with distilled water. This entire process will result in complete hydroxylation of the SiO2 surface to form a silicon hydroxide (SiOH) surface. The resulting SiOH substrate will be dried with nitrogen gas and kept at −20° C. for further use. Next maleimide-terminated SAMs are synthesized on SiOH substrate. The SiOH substrate will be treated with 1M solution of 3-aminopropyltrimethoxysilane in ethanol for 1 hr simply by a dipping process. This will result in the formation of amine (—NH2) terminated self-assembly monolayers (SAMs). This —NH2 terminated SAMs can readily react with activated carboxyl acid for further modification of the surface. In a preferred embodiment, the —NH2 terminated SAMs will be incubated with 1 M solution of succinimidyl-4-(N-maleimidomethyl)cyclohexane-1-carboxylate (SMCC) in dimethylsulfoxide (DMSO) for 2 hrs, followed by washing out the unreacted compounds with distilled water. This process will result in the formation of SAMs with maleimide terminated functional surface groups. These maleimide-terminated SAMs can then spontaneously react with any type of biomolecules that have one or more free thiol functional groups such as proteins, peptides, half-antibodies and other antibody fragments, and thus immobilize the biomolecules onto the substrate surface. To prepare clean and high quality SAMs, the formed SAMs need to be washed with distilled water and dried under continuous flow of nitrogen gas, and then stored at −20 C for future use. As it is cleaned with MeOH/HCl (1/1) for 30 min at room temperature, rinsed with ultra pure water (Milli-Q Gradient A10 18.2 MΩ, and dried with Argon. In the next step, the surface is modified with NH2 groups by a silanization step with 3-aminopropyltriethoxysilane (APTES) either in the gas phase or in the liquid phase. For gas-phase silanization, the chips are placed in a desiccator containing a few drops of silane. The desiccator is sealed and heated above 100° C., and the chips were left to react for 1-2 h under a low pressure (~1 mbar) with the silane vapor.

"Surface Characterization" as used herein refers to the methods such as Atomic Force Microscopy (AFM), Scanning Electron Microscopy (SEM), and X-ray Photoelectron Spectroscopy (XPS). The evidence of each steps of the formation of SAMs can be monitored by using Fourier transfer inferred (FT-IR) spectroscopic, which will provide characteristic signal of the functional groups in the SAMs.

"Target Analyte," as used herein refers to the substance to be detected in the test sample using the present invention. The analyte can be any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, antibodies, and combinations thereof. The target analyte can include a protein, a peptide, an amino acid, a carbohydrate, a hormone, asteroid, a vitamin, a drug including those administered for therapeutic purposes as well as those administered for illicit purposes, a bacterium, a virus, and metabolites of or antibodies to any of the above substances "Target Analyte-Analog" as used herein refers to a substance which cross reacts with an analyte capture reagent although it may do so to a greater or lesser extent than does the target analyte itself. The target analyte-analog can include a modified target analyte as well as a fragmented or synthetic portion of the target analyte molecule so long as the target analyte analog has at least one epitomic site in common with the target analyte of interest.

"Capture Reagent," as used herein refers to a molecule or compound capable of binding the target analyte or target reagent, which can be directly or indirectly attached to a substantially solid material. The capture agent can be any substance for which there exists a naturally occurring target analyte (e.g., an antibody, polypeptide, DNA, RNA, cell, virus, etc.) or for which a target analyte can be prepared, and the capture reagent can bind to one or more target analytes in an assay.

"Test Sample" as used herein refers to the sample containing the target analyte to be detected and assayed using the present invention. The test sample can contain other components besides the target analyte, can have the physical attributes of a liquid, or a solid, and can be of any size or volume, including for example, a moving stream of liquid. The test sample can contain any substances other than the target analyte as long as the other substances do not interfere with the binding of the target analyte with the capture reagent or the specific binding of the first binding member to the second binding member. Examples of test samples include, but are not limited to: Serum, plasma, sputum, seminal fluid, urine, other body fluids, and environmental samples such as ground water or waste water, soil extracts, air and pesticide residues.

"Methods and Reagents" as used herein refers to (For the propose of analysis and testing of the proposed apparatus the authors employ and use the information provided by HS Lee et al., 2008 paper for the propose of identifying the methods) reagents such as: 3-Aminopropyl diethoxysilane (APDES), succinic anhydride (SA), sodium carbonate (SC), phosphate buffered saline (PBS) tablet, sodium dodecylsulfate (SDS), 1-ethyl-3-[3-(dimethylamino) propyl]carbodiimide (EDC), N-hydroxysulfo succinimide (sulfo-NHS), sodium hydroxide (NaOH), sodium chloride (NaCl) (Sigma-Aldrich Co. St. Louis, Mo.). As a detecting protein, human VEGF165 Cell (Signaling Technology, Inc. Danvers, Mass.). The human VEGF165 coding cDNA is reported to be sub cloned into an expression vector and expressed in yeast. The recombinant human VEGF165 homodimer is reported as further purified and stored in phosphate buffered saline (PBS, pH 7.4) containing 0.1% BSA.

"Synthesis of Anti-VEGF Monoclonal Antibody" as used herein refers to a humanized anit-VEGF antibody is cut into half by mean of chemical process. Tris(2-carboxyethyl) phosphine (TCEP) with a molar excess of 3× over the molar concentration of the anti-VEGF monoclonal antibody (mAb) will be used as reduction agent. The TCEP reduction agent will be mixed with the anti-VEGF mAb in PBS buffer for 2 hrs at room temperature. The TCEP will selectively cleave the disulfide bonds that connecting the two heavy chains of a mAB and produces two anti-VEGF half-antibody (hAb). The resulting hAb possess intact binding sites and reactive thiol groups. These hAb retain their targeting ability but are smaller in size and can be conjugated in a site-specific manner. In the study, the resulting hAb can be directly used, without prior purification, to react with the maleimide-terminated SiO2 surface.

"Characterization of Anti-VEGF Monoclonal Half-Antibody" as used herein refers to the confirmation of the synthesized half-antibody. The selective reduction process will be optimized using sodium dodecyl sulfate polyacrylamide gel electrophoresis (SDS-PAGE). To confirm the production of hAb and to optimize the selective reduction process, anti-VEGF mAb will be mixed with different molar excess of TCEP for 2 hrs and then separated and visualized. Specifically, the cleaved mAb will be separated on a SDS-PAGE 3-8% Tri-Acetate 10-well mini gel in tri-acetate running buffer using NovexSureLockXcell Electrophoresis System (Invitrogen). The samples will be run at 150V for 1 hr and the resulting polyacrylamide gel will be stained in SimplyBlue™ (Invitrogen) overnight for visualization. To quantify the hAb concentration, Alexa Fluor 488 fluorescence probe can be pre-conjugated to the mAb prior to the reduction. Then the fluorescence intensity from the hAb can be measured and compared to a standardization curve.

"Binding Affinity of Synthesized Anti-VEGF Half-Antibody" as used herein refers to the use of surface plasmon resonance (SPR) analyses (Kang et al., 2008) for analyzing interactions between two biomolecules.

"A Homeostatic Control Mechanisms" as used herein refers to the concept that at least three interdependent components of the biosensor's measured-variables are being regulated: The receptor is the sensing component, (hybridized VEGF molecule that change the capacitive load, hence, monitors and responds to changes in the environment. The receptor senses a stimulus; it sends information to a control circuit, the component that sets the range at which a variable is maintained. The control circuit determines an appropriate response to the stimulus. The control circuit then sends signals to an effector which that receive signals from the control circuit. After receiving the signal, a change occurs to correct the deviation by either enhancing it with positive feedback or depressing it with negative feedback.

"Angiogenesis" as used herein refers to a physiological process involving the growth of new blood vessels from pre-existing vessels. Though there has been some debate over terminology, vasculogenesis is the term used for spontaneous blood-vessel formation, and intussusception is the term for new blood vessel formation by splitting off existing ones.

"Signal Transduction" as used herein refers to a mechanism that converts a mechanical/chemical stimulus to a cell into a specific cellular response. Signal transduction starts with a signal to a receptor, and ends with a change in cell function.

"Tyrosine Kinase" as used herein refers to an enzyme that can transfer a phosphate group from ATP to a tyrosine residue in a protein. Tyrosine kinases are a subgroup of the larger class of protein kinases. Phosphorylation of proteins by kinases is an important mechanism in signal transduction for regulation of enzyme activity.

"Microelectromechanical systems (MEMS)" as used herein refers to the technology of the very small, and merges at the nano-scale into nanoelectromechanical systems (NEMS) and nanotechnology. MEMS are made up of components between 1 to 100 micrometers in size (i.e. 0.001 to 0.1 mm) and MEMS devices generally range in size from 20 micrometers (20 millionths of a meter) to a millimeter. They usually consist of a central unit that processes data, the microprocessor and several components that interact with the outside such as microsensors.

"Oligonucleotide" as used herein refers to a short nucleic acid polymer, typically with twenty or fewer bases. Although they can be formed by bond cleavage of longer segments, they are now more commonly synthesized by polymerizing individual nucleotide precursors. Automated synthesizers allow the synthesis of oligonucleotides up to 160 to 200 bases.

"Lectins" as used herein refers to sugar-binding proteins that are highly specific for their sugar moieties. They play a role in biological recognition phenomena involving cells and proteins. For example, some viruses use lectins to attach themselves to the cells of the host organism during infection.

"Aptamers" as used herein refers to oligonucleic acid or peptide molecules that bind to a specific target molecule. Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications.

"Peptides" as used herein refers to short polymers formed from the linking, in a defined order, of α-amino acids. The link between one amino acid residue and the next is called an amide bond or a peptide bond.

"Resonance" as used herein refers to the tendency of a system to oscillate at larger amplitude at some frequencies than at others. These are known as the system's resonant frequencies (or resonance frequencies). At these frequencies, even small periodic driving forces can produce large amplitude oscillations.

"Quartz Crystal Microbalance (QCM)" as used herein refers to device which measures a mass per unit area by measuring the change in frequency of a quartz crystal resonator. The resonance is disturbed by the addition or removal of a small mass due to oxide growth/decay or film deposition at the surface of the acoustic resonator.

"Enzymes" as used herein refers to proteins that catalyze (i.e., increase the rates of) chemical reactions. In enzymatic reactions, the molecules at the beginning of the process are called substrates, and the enzyme converts them into different molecules, called the products. Almost all processes in a biological cell need enzymes to occur at significant rates. Since enzymes are selective for their substrates and speed up only a few reactions from among many possibilities, the set of enzymes made in a cell determines which metabolic pathways occur in that cell.

"Epitope" as used herein refers to the part of an antigen that is recognized by the immune system, specifically by antibodies, B cells, or T cells. The part of an antibody that recognizes the epitope is called a paratope. Although epitopes are usually thought to be derived from non-self proteins, sequences derived from the host that can be recognized are also classified as epitopes.

"Self Assembled Monolayer (SAM)" as used herein refers to an organized layer of amphiphilic molecules in which one end of the molecule, the "head group" shows a special affinity for a substrate. SAMs also consist of a tail with a functional group at the terminal end. SAMs are created by the chemisorption of hydrophilic "head groups" onto a substrate from either the vapor or liquid phase followed by a slow two-dimensional organization of hydrophobic "tail groups". Initially, adsorbate molecules form either a disordered mass of molecules or form a "lying down phase", and over a period of hours, begin to form crystalline or semicrystalline structures on the substrate surface. The hydrophilic "head groups" assemble together on the substrate, while the hydrophobic tail groups assemble far from the substrate. Areas of close-packed molecules nucleate and grow until the surface of the substrate is covered in a single monolayer.

"Biological Response Modifiers (BRMs)" as used herein refers to substances that the human body produces naturally, as well as something that scientists can create in a lab. These substances arouse the body's response to an infection. Some of these are used to treat arthritis, cancer, and some other diseases. Immunotherapy makes use of BRMs to enhance the activity of the immune system to increase the body's natural defense mechanisms against cancer, whereas BRMs for rheumatoid arthritis aim to reduce inflammation.

"Medical Implant Communication Service (MICS)" as used herein refers to the name of a specification for using a frequency band between 402 and 405 MHz in communication with medical implants. It allows bi-directional radio communication with a pacemaker or other electronic implants. The maximum transmit power is very low, EIRP=25 microwatt, in order to reduce the risk of interfering with other users of the same band. The maximum used bandwidth at any one time is 300 kHz, which makes it a low bit rate system compared with WiFi or Bluetooth. The main advantage is the additional flexibility, compared to previously used inductive technologies, which required the external transceiver to touch the skin of the patient. MICS gives a range of a couple of meters.

"Capacitor" as used herein refers to a passive electronic component consisting of a pair of conductors separated by a dielectric (insulator). When a potential difference (voltage) exists across the conductors, an electric field is present in the dielectric. This field stores energy and produces a mechanical force between the conductors. The effect is greatest when there is a narrow separation between large areas of conductor, hence capacitor conductors are often called plates.

DETAILED DESCRIPTION OF THE INVENTION

FIG. 1 is an orthographic cross sectional view of the apparatus with a schematic representation of the electronic detection module. The biosensor with its insulating enclosure 100. The enclosure 100, is configured with fluid flow inlet 101, and a flow outlet 102. The apparatus 100 includes an array of electrodes coated with VEGF sensing elements which form the capacitive plates 103, which are interfaced with the electronic module 200, and forms the VEGF capacitance detector circuit. The VEGF capacitance detector circuit is connected to an operational amplifier (OpAmp) buffer 201, and a current-to-voltage amplifier 202 followed by an OpAmp integration circuit 203, including biasing resistors 204, 205, and capacitor 206. The input voltage Vin 207, and current output 1209, with V1 209 represent the respective potential after hybridization and the resulting integral value of the capacitive change in the circuit 200. The electrodes are designed as an interdigitated pattern in order to maximize the sensor surface area in a small volume.

Figure 1A:
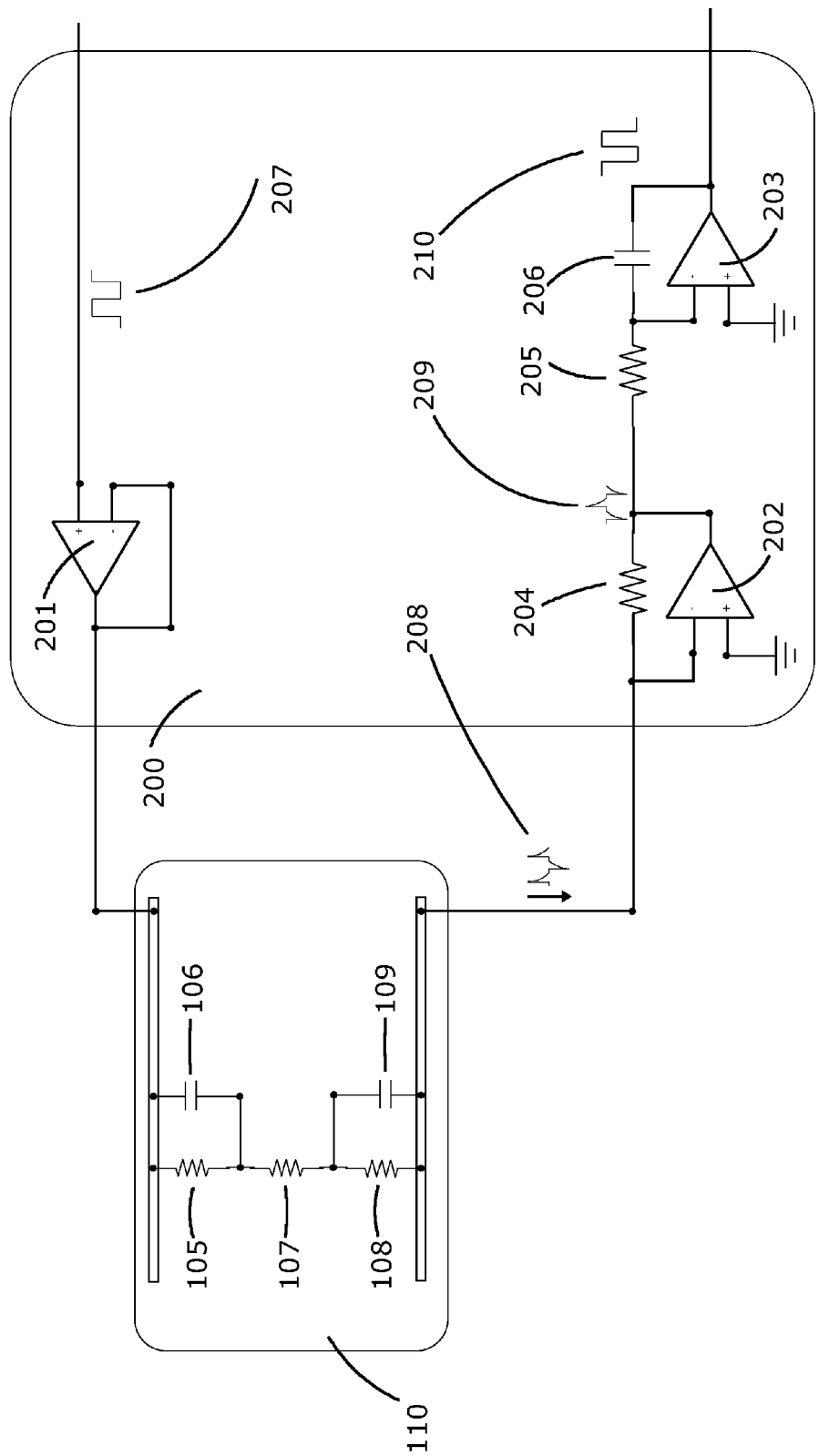
FIG. 1A is a electrical schematic representation of an embodiment of the invention depicting one cell of an equivalent electrode-electrolyte node from the capacitor array.

FIG. 1A is a schematic representation of an embodiment of FIG. 1 depicting one cell of the an equivalent electrode-electrolyte node which forms the capacitor array 110. The circuit schematic 110 is represented as depicting the resistance of electrode a/solution interface ($R_a$) by resistance 105, and its capacitive load Ca 106. The resistance of the solution within the sensor body 100, is represented by ($R_s$) 107, while the resistance of electrode B/solution interface ($R_b$) 108 and its capacitive load ($C_b$) 109. The one-nodal unit of the array capacitor forming the biosensor 110, is interfaced with the capacitive detector circuit 200. A square wave generator constitute the input ($V_{in}$) signal 207 is buffered by the OpAmp 201, and results in current 208, representing the respective attenuated value of the circuit after the hybridization of the VEGF binding with the a-VEGF mhAb, $R_1$ 204. Current 208 is coupled to the OpAmp acting as current-to-voltage amplifier 202 to indicate the respective integral value of the capacitive cell 110, after the capacitive change due to the binding of the VEGF molecule with the a-VEGF mhAb shown by the equivalent circuit node 110. The signal is further integrated by an OpAmp 203, and its associated resistor 205, capacitor 206 resulting in output voltage ($V_{out}$) 210.

Figure 2:
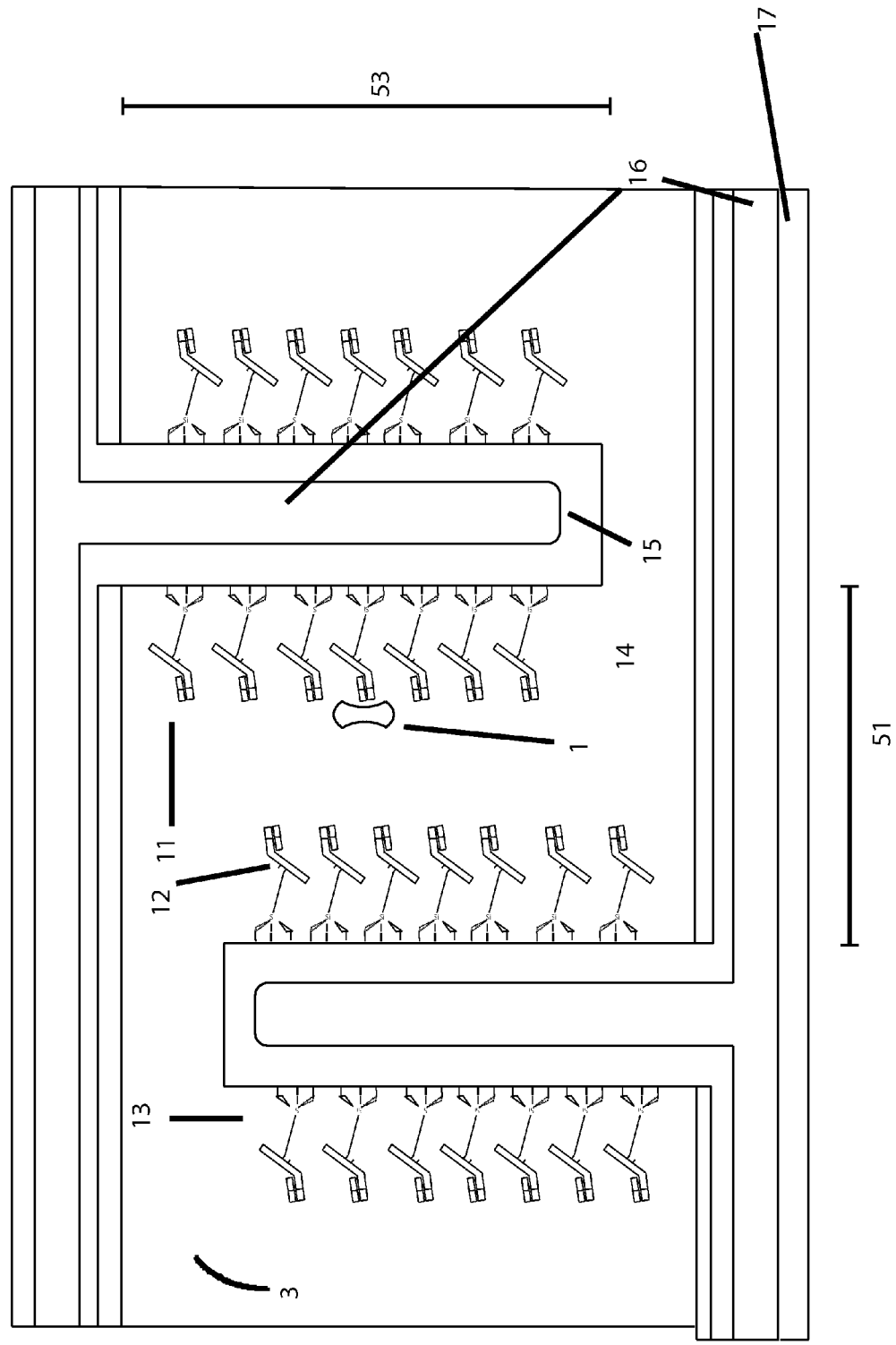
FIG. 2 is a cross sectional isometric view of the capacitive arrangement of the VEGF detector.

FIG. 2 is a cross section of an isometric view of the capacitive arrangement of the VEGF detector. The figure depicts the elements noted in FIGS. 1 and 1A, which further explain and clarify the relationship between the equivalent electronic module 110, and the sensing principles that govern the performance of the VEGF detector. The VEGF biosensor is based on an electrochemical approach, whereby a capacitor with geometry $G_{x\ 300}$, is employed with the aim of using the dielectric ($\in_r$) in Equation 1, below, as a variable and further exploiting a label-free detection technique based on capacitance measurements of bio-modified electrode/solution interfaces. The sensor 100 function is best defined by the ability of the sensor to effectively immobilize the stranded a-VEGF mhAb 11, on conducting electrode surfaces 16. The electrolyte solution (the medium between the electrodes) is a bodily fluid such as cerebrospinal fluid 3. The electrode 16, is coated with a p-Si substrate 15, to enhance the affinity between VEGF 1, and the a-VEGF mhAb 11. An insulation layer (e.g.

silicon dioxide) 14, protects the positively charged substrate 15, which is bonded with a linker (Succinimidyl-4-(N-maleimidomethyl)cyclohexane-1-carboxylate) 12, via a hybridization substance (3-aminopropyl-trimethoxysilane) 13. The a-VEGF mhAb are then immobilized by bonding with the linker. The total increase in surface thickness due to the immobilization of the a-VEGF mhAb is about 10 nm. When the VEGF proteins 1, are introduced in the bodily fluid 3, they bind to the electrode surfaces coated with a-VEGF mhAb. The binding of the VEGF molecules and a-VEGF mhAb changes the impedance (i.e. mainly its capacitance) of the electrode-solution interface. When the VEGF molecules hybridize with a-VEGF mhAb at its Anti-VEGF fragment, antigen binding (Fab) region interface 10, the total thickness is about 200 nm.

The capacitances 106 and 109 of the electrochemical cell 110 can be modeled as shown in Equation 1.

$$C_{cell} = C_{geometry} + C_{electrode/solution} \quad (1)$$

Where $C_{Geometry}$ is the capacitance due to the geometry of the sensor as shown in Equation 2.

$$C_{geometry} = \epsilon_r \epsilon_0 A/d \quad (2)$$

Where $\epsilon_r$ is the combined relative permittivity, (dielectric constant," $\epsilon_r$. $[-(\epsilon_r)_1, (\epsilon_r)_2, \ldots (\epsilon_r)_n]$, of the dielectric value of the combined medium prior to hybridization and is considered the value of the total capacitance "$C_{cell}$"), of the medium consisting of VEGF molecules, bodily fluid, a-VEGF mhAb, Succinic linker, Amino hybridization substance, $SiO_2$ insulator, and p-Si substrate; $\epsilon_0$ is the permittivity of the free space ($8.854 \times 10^{-12}$ F/m); A is the total area given by width 52 and length 53 of the electrode plates 103, and d is the separation 51 between the plates 103. The values of A and d are chosen so that the change in capacitance can be effectively measured with the following technique, but the circulation flow of the body fluid through the sensor unit 100 is unrestricted. Due to the fact that the thickness of the surface when VEGF binds is about 200 nm, the separation can be as small as 5000 nm without the risk of restricting the flow due to VEGF hybridization. The electrode plates 103, are arranged in an interdigitated fingers pattern so that effective surface area is maximized in a small volume. The body fluid 3 flows into the sensor unit via an inlet 101, and outlet 102, and possibly connected to a pump and valve arrangements as shall be further described in FIG. 5.

$C_{electrode/solution}$ is double layer capacitance formed between each of the two electrodes and the solution. This double layer capacitance can be modeled as shown in Equation 3, below. $C_{electrode/solution}$ is represented by $C_A$ and $C_B$ in Equations 9 and 10 below for electrodes A and B.

$$\frac{1}{C_{electrodalsolution}} = \frac{1}{C_{insulator}} + \frac{1}{C_{linker}} + \frac{1}{C_{Macugen}} + \frac{1}{C_{VEGF}} \quad (3)$$

The total value of $C_{cell}$ is approximately 1 µF/cm$^2$ with a dynamic range of about 0.3 µF/cm$^2$ when all a-VEGF mhAb are bonded with VEGF.

Figure 2A:
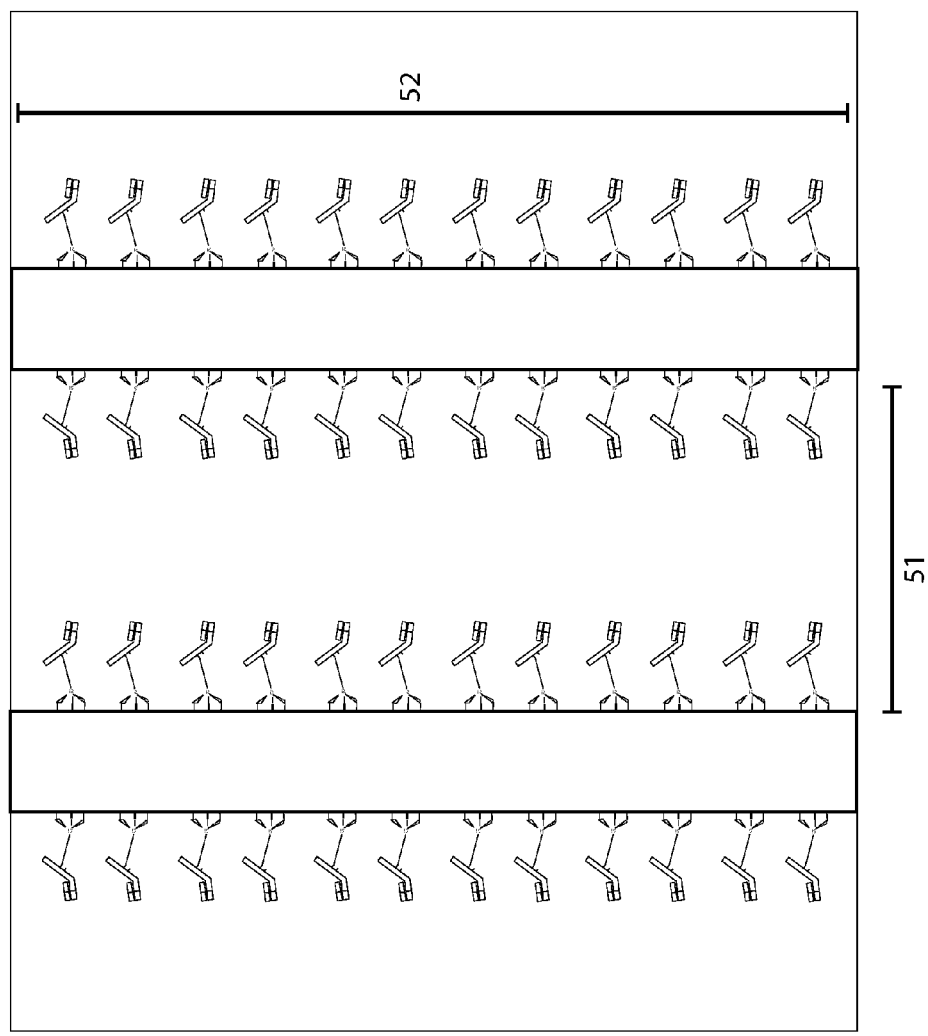
FIG. 2A is a top view of an orthographic representation of the capacitive VEGF sensor.

FIG. 2A is a top view of an orthographic representation of the capacitive VEGF sensor, whereby the capacitor plates 103 are represented as to their respective effective geometrical terms $G_x$ 300. The values of A and d are chosen so that the change in capacitance can be effectively measured with the following technique. The boundary conditions for the selection of the dimensions 51 [($d_{cap}$), the distance between the sensor plates in calculating the capacitance value], and 52 [($W_{cap}$), the width of the sensor plates 103 used to calculate the capacitance value] are defined by providing an unrestricted circulation flow of the body fluid through the sensor unit 100, and by setting the hydrostatic flow rate at a constant value.

The measurement technique of the electrochemical cell, as noted by FIGS. 1, 1A, 2, & 2A, is based on the sensing principle of a variable capacitor cell where the dielectric ($\epsilon_r$) of the electrode/solution interface model 110 is the variable. In this model, the VEGF protein 1, stranded on an a-VEGF mhAb 11, introduces additional insulating layers 14, between electrode and solution, resulting in a measurable change in capacitive component of the interface model. The charge-based capacitance measurement (CBCM) technique can measure this change in capacitive component of the electrode-solution interface impedance. The measurement principle of this CBCM technique is to charge and discharge the VEGF electrochemical cell at an appropriate frequency, and measure its equivalent capacitance from the average current in half-period, noted in Equation 4.

$$I_{avg} = \frac{\Delta Q}{T/2} = \frac{C\Delta V}{T/2} = 2C\Delta Vf \quad (4)$$

Where $\Delta V$ and f are known and $I_{avg}$ can be measured. This measurement technique is illustrated in circuit 200, which consists of two separate circuits. The OpAmp voltage follower 201 increases the input impedance of the electrochemical cell so that the cell can be driven by a near perfect square wave 207 from a digital output signal line from a microcontroller 401. The frequency (f) of the square wave is chosen as the maximum frequency that completely charges and discharges the capacitor in the electrochemical cell in the half period.

The second part of circuit 200, converts $I_{avg}$ 208, into voltage value with a known resistor value $R_1$ 204, and amplified by an Op-Amp 202. $V_1$ 209, at the output of the Op-Amp 202, can be calculated as shown in Equation 5.

$$V_1 = -C_{cell} R_1 \frac{dV_{in}}{dt} \quad (5)$$

An Op-Amp integration circuit 203 converts the transient voltage values 209, into a square wave 210, as shown in Equation 6.

$$V_{out} = -\frac{1}{C_2} \int \frac{V_1}{R_2} dt \quad (6)$$

Substituting Equation 2 into 3, the output of circuit 200, as a function of its input can be calculated as shown in Equation 7 leading to Equation 8.

$$V_{out} = -\frac{1}{C_2 R_2} \int -C_{cell} R_1 \frac{dV_{in}}{dt} dt \quad (7)$$

$$V_{out} = \frac{C_{cell} R_1}{C_2 R_2} V_{in} \quad (8)$$

The output voltage of circuit 200, which is sampled by an ADC 402, is proportional to the value of $C_{cell}$.

FIG. 3 is a graphic depiction of the VEGF sensor with its constituent hybridization elements, and where an immobilized a-VEGF mhAb 11, (through Fab fragments that are selected for high-affinity binding to molecular targets, the concept of using a single-stranded antibody as affinity molecules for protein binding was initially described in 1998 (Y A Muller et al, 1998), and is based on the ability of short sequences to fold, in the presence of a target, into unique, three-dimensional structures that bind the target with high affinity and specificity. One half of a-VEGF mAb 21, for example Avastin®, is used due to its proven binding affinity to VEGF molecules 1. A-VEGF mhAb 11 is attached to a linker 12, [Succinimidyl-4-(N-maleimidomethyl)cyclohexane-1-carboxylate, also called 4-(N-Maleimidomethyl)cyclohexanecarboxylic acid N-hydroxysuccinimide ester, is an organic compound with the molecular formula $C_{16}H_{18}N_2O_6$]. The linker 12, is attached to a hybridization substance (3-aminopropyl-trimethoxysilane), employing biocompatible scaffolds to provide viable alternatives forming the prosthetic materials for adhesion. The use of maleimide-terminated SAMs, 20, as scaffold to grow the linker 12, is advantageous because of its high surface area, which permits a large number of sites for the succinic anhydride 12, adhesion and growth. This —$NH_2$ terminated SAMs can readily react with activated carboxyl acid for further modification of the surface. The linker 12, is further combined with a hybridization substance (3-aminopropyl-trimethoxysilane) 13. The surface of a quartz or glass wafer ($SiO_2$ 14) is treated with different aminosilanes in solution where surface density increased sharply with the reaction time and produced the multilayer. The amino-silanization 13, are scaffolds that provide viable alternatives forming the prosthetic materials for adhesion to the $SiO_2$ insulator surface 14. The immobilized a-VEGF mhAb 11 complex is used to detect circulating VEGF isoform 1.

The fabrication of silicon insulator surface is detailed by HS Lee et al., 2008 which describes a layer of Au (100 µm) deposited to form the interleaved array of electrodes 103, inside an insulating enclosure 17. Silicon crystal for p-doping 15 is grown on the Au conductor surface 16, with a constant flow of $SiH_4$ precursor at 530 C under the gas pressure of 50 Torr. During this process, silicon crystals are in situ doped with $B_2H_6$ as p-dopants at the relative pressure ratio of $SiH_4$:$B_2H_6$ to be $10:1\times10^{-3}$. The flow of $SiH_4$ is continued but $B_2H_6$ is stopped when the p-substrate 15, reaches 1 µm. After the additional Si layer reaches 10 nm, the flow of $SiH_4$ is stopped; the temperature is raised to 820° C. and gas chamber is opened to the atmospheric pressure, allowing oxidation in the dry atmosphere to form the $SiO_2$ insulation layer 14.

Therefore, the combined thickness of one sensor plate is 102.02 µm (the sum of the thicknesses of electrode, two layers of p-substrate, two layers of insulator). With d (the distance between the plates 51) as 50 µm, the total space required for each electrode pair is 152.02 µm. Because the plate area of 1 $cm^2$ provides sufficient capacitance of around 1 µF, A is chosen as 1 $cm^2$ and W (the width of the plates 52) is arbitrarily chosen as 0.5 cm, which leads to the total length of the plates to be 2 cm or 20000 µm. With L (the length of the plates 53) chosen as 1000 µm, there are 20 turns or electrode pairs arranged in interdigitated finger pattern. Thus, the total volume of the sensor is 5000 µm×1000 µm×3040.4 µm.

Figure 3A:
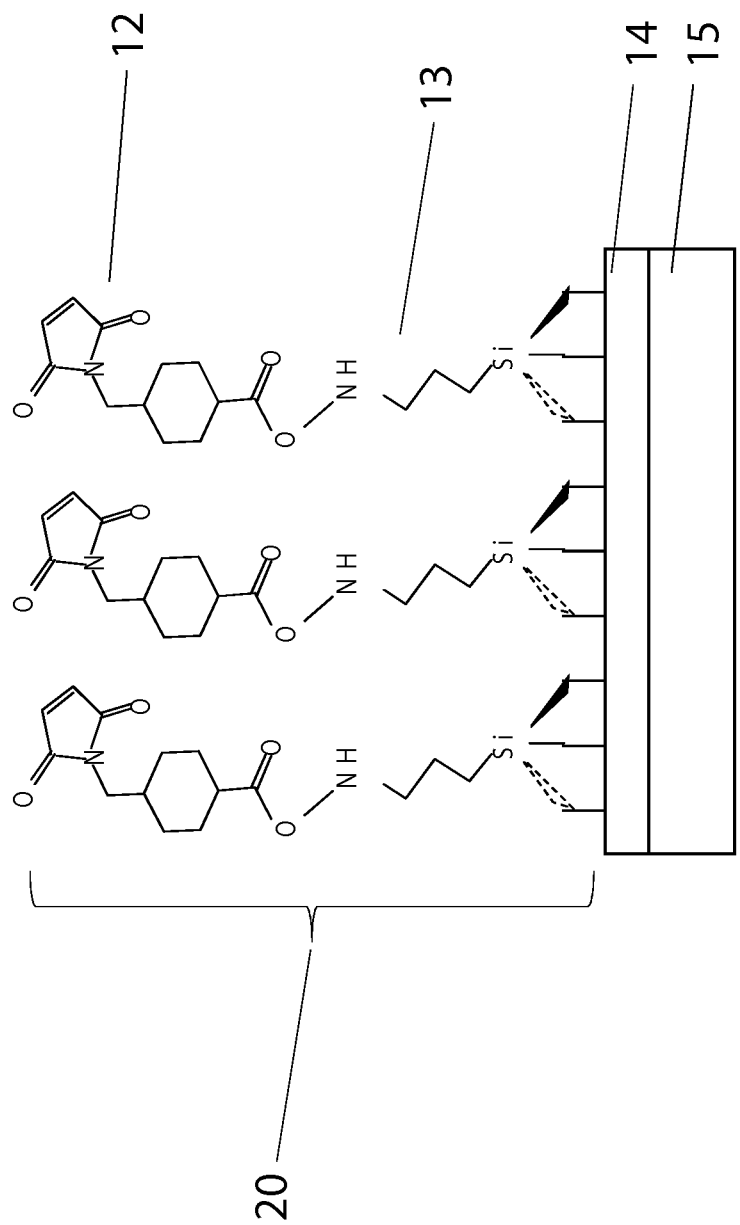
FIG. 3A is a graphic depiction of the Maleimide-terminated SAMs prior to functionalizing by anti-VEGF monoclonal half-antibody (a-VEGF mhAb).

FIG. 3A is a graphic depiction of the maleimide-terminated SAMs prior to functionalizing by anti-VEGF monoclonal half-antibody (a-VEGF mhAb). The fundamental characterization of SAMs can be done by using surface characterization techniques such as Atomic Force Microscopy (AFM), Scanning Electron Microscopy (SEM), and X-ray Photoelectron Spectroscopy (XPS). The evidence of each steps of the formation of SAMs can be monitored by using Fourier transfer inferred (FT-IR) spectroscopic, which provides characteristic signal of the functional groups in the SAMs.

Figure 3B:
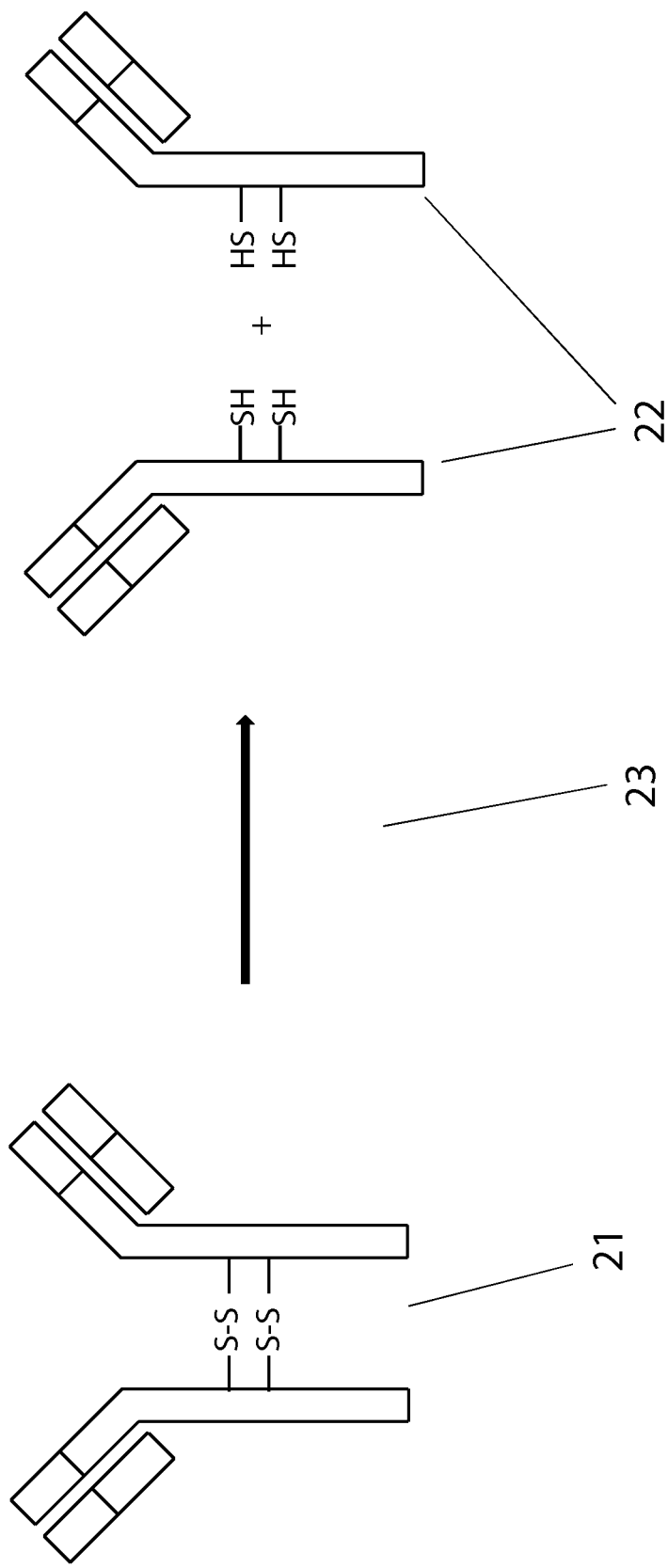
FIG. 3B is a graphic representation of the selective reduction process to split the anti-VEGF monoclonal antibody (a-VEGF mAb) into two half-antibodies.

FIG. 3B is a graphic representation of the selective reduction process to split the anti-VEGF monoclonal antibody (a-VEGF mAb) into two half-antibodies. The figure illustrates that tris(2-carboxyethyl) phosphine (TCEP) with a molar excess of 3× over the molar concentration of the anti-VEGF monoclonal antibody (mAb), 21, is used as reduction agent. The TCEP reduction agent is mixed with the anti-VEGF mAb in PBS buffer for 2 hrs at room temperature. The TCEP selectively cleave the disulfide bonds that connecting the two heavy chains of a mAB and produces two anti-VEGF half-antibody (hAb), 22. The resulting hAb possess intact binding sites and reactive thiol groups. These hAb retain their targeting ability but are smaller in size and can be conjugated in a site-specific manner. In one embodiment, the resulting hAb can be directly used, without prior purification, to react with the maleimide-terminated $SiO_2$ surface.

In an embodiment, the selective reduction process is optimized by using sodium dodecyl sulfate polyacrylamide gel electrophoresis (SDS-PAGE). To confirm the production of hAb and to optimize the selective reduction process, a solution containing a-VEGF mAb is mixed with different molar excess of TCEP for 2 hrs and then separated and visualized. Specifically, the cleaved mhAb are separated on a SDS-PAGE 3-8% Tri-Acetate 10-well mini gel in tri-acetate running buffer using NovexSureLockXcell Electrophoresis System (Invitrogen). The samples are run at 150V for 1 hr and the resulting polyacrylamide gel is stained in SimplyBlue™ (Invitrogen) overnight for visualization. To quantify the hAb concentration, Alexa Fluor 488 fluorescence probe can be pre-conjugated to the mAb prior to the reduction. Then the fluorescence intensity from the hAb can be measured and compared to a standardization curve.

Figure 3C:
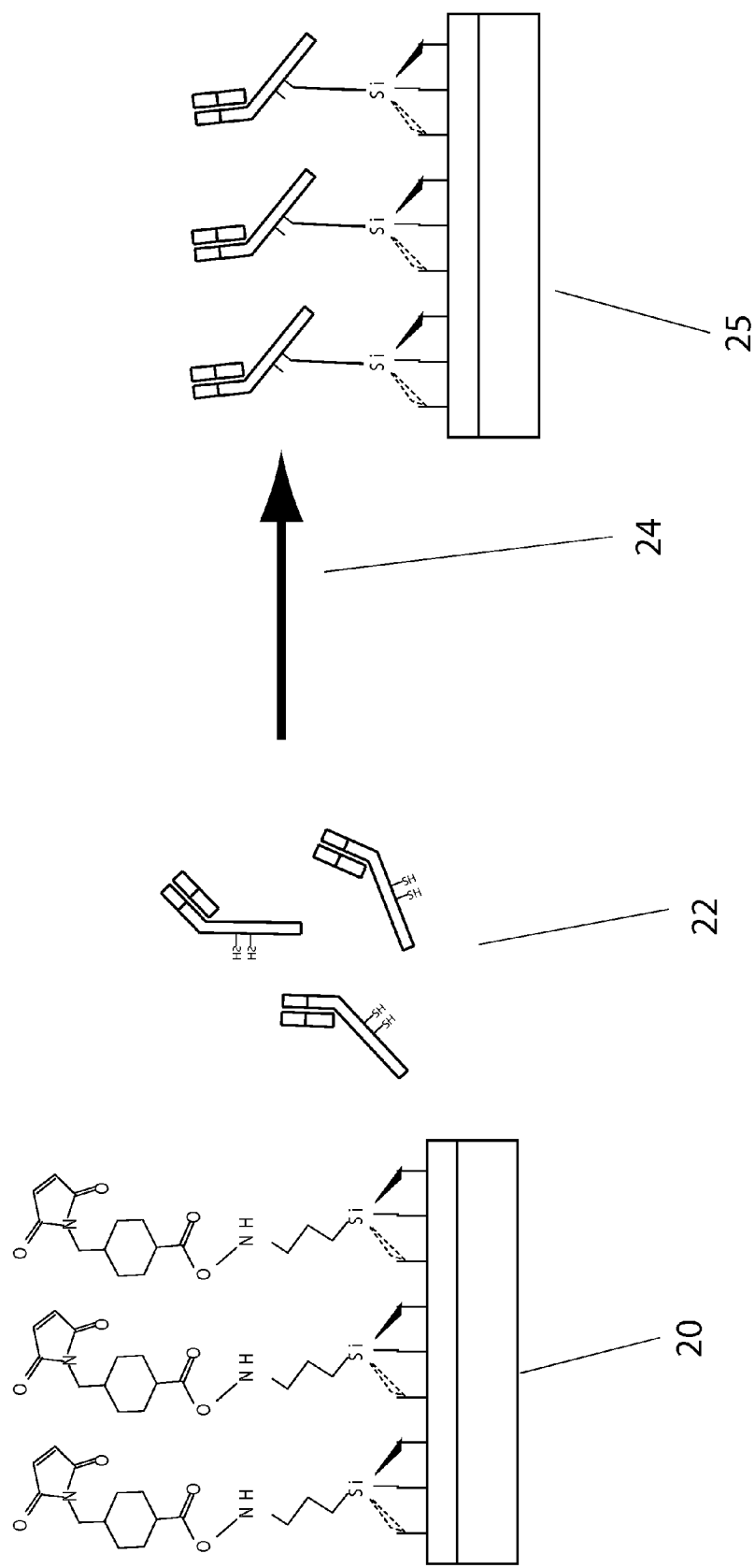
FIG. 3C is a graphic representation of a spontaneous reaction involving Maleimide-thiol conjugation to produce a-VEGF mhAb functionalized $SiO_2$ substrate.

FIG. 3C is a graphic representation of a spontaneous reaction involving maleimide-thiol conjugation to produce a-VEGF mhAb functionalized $SiO_2$ substrate, 25. Maleimide-thiol coupling occurs rapidly and spontaneously. The maleimide-terminated $SiO_2$ substrate 20, is incubated with a-VEGF mhAb 22, solution at a desirable concentration for 2 hrs. The a-VEGF mhAb 22, spontaneously couple to the substrate surface in an orientation-specific manner. As illustrated in the figure, the antigen-binding site is kept toward outside. The concentration of the a-VEGF mhAb 22, is used to control the hAb coating density on the substrate. After incubation, the substrate is rinsed with PBS buffer to remove all unconjugated compounds.

In one embodiment, the coupling reaction is confirmed and quantified using fluorescence measurements. Before TCEP reduction, a-VEGF mhAb are covalently labeled with Alex-488 fluorophores. To confirm that the retained fluorescence is due to maleimide-thiol conjugation rather than non-specific absorption of a-VEGF mhAb or uncleaved mAb, intact mAb are used as a negative control to ensure that mAb does not absorb and stick to the substrate after rinsing with PBS buffer. Next, VEGF proteins are used to further evaluate the binding sensitivity and specificity of the immobilized anti-VEGF hAb.

Figure 4:
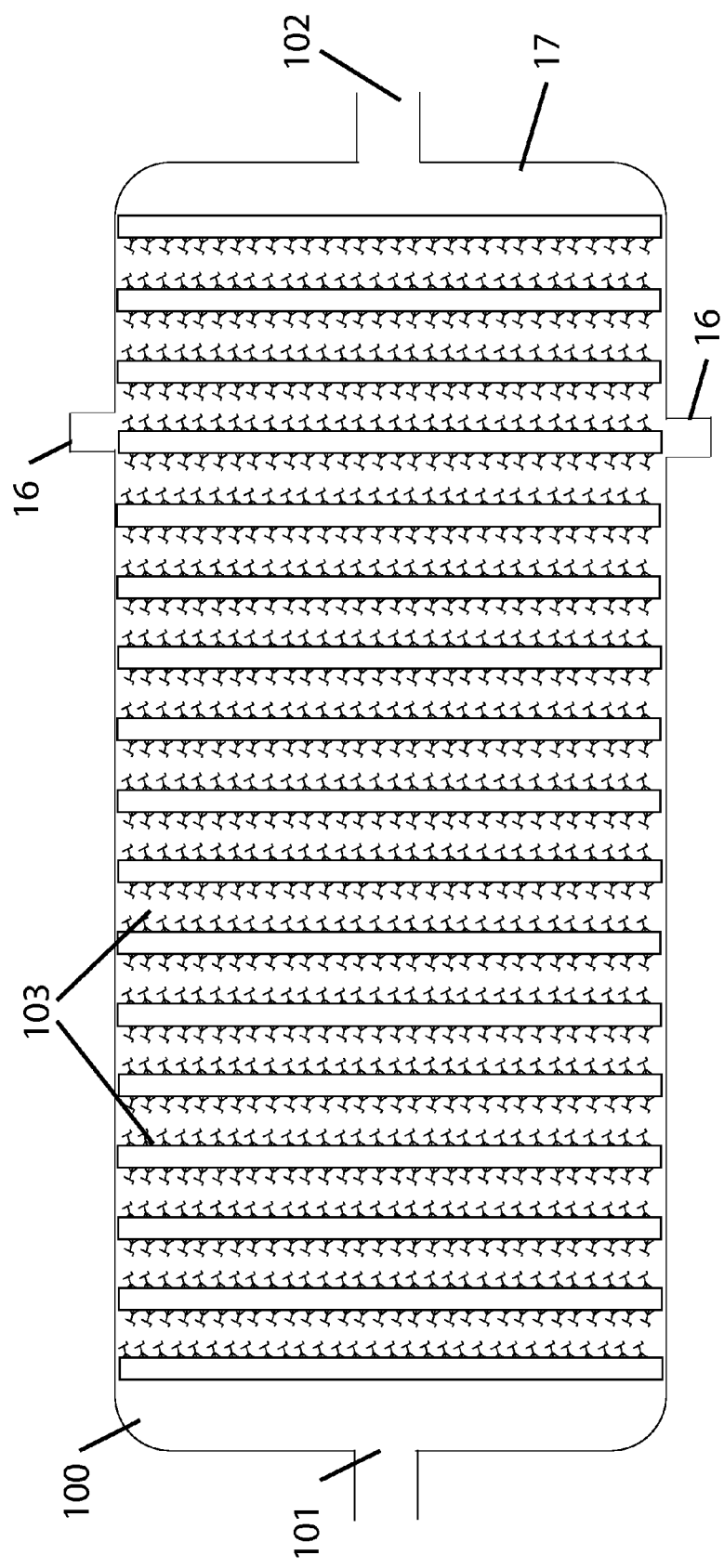
FIG. 4 is a cross sectional view of the biosensor capacitor array with its matrix array layout including the chamber containment.

FIG. 4 is a cross sectional top view of the biosensor 100, formed as capacitor with its electrode matrix array 103, and the layout including the containment enclosure 17. The biosensor contains an array of electrodes coated with VEGF sensors forming capacitive plates 103, so as to maximize the response of the capacitive change in the circuit, by providing the largest surface area within the parameter of the biochip enclosure 17. The figure further illustrates the fluid flow inlet 101, and the flow outlet 102, the electrical interface 16, and the insulating enclosure 17 is depicted as the parameters of the proposed device.

Figure 4A:
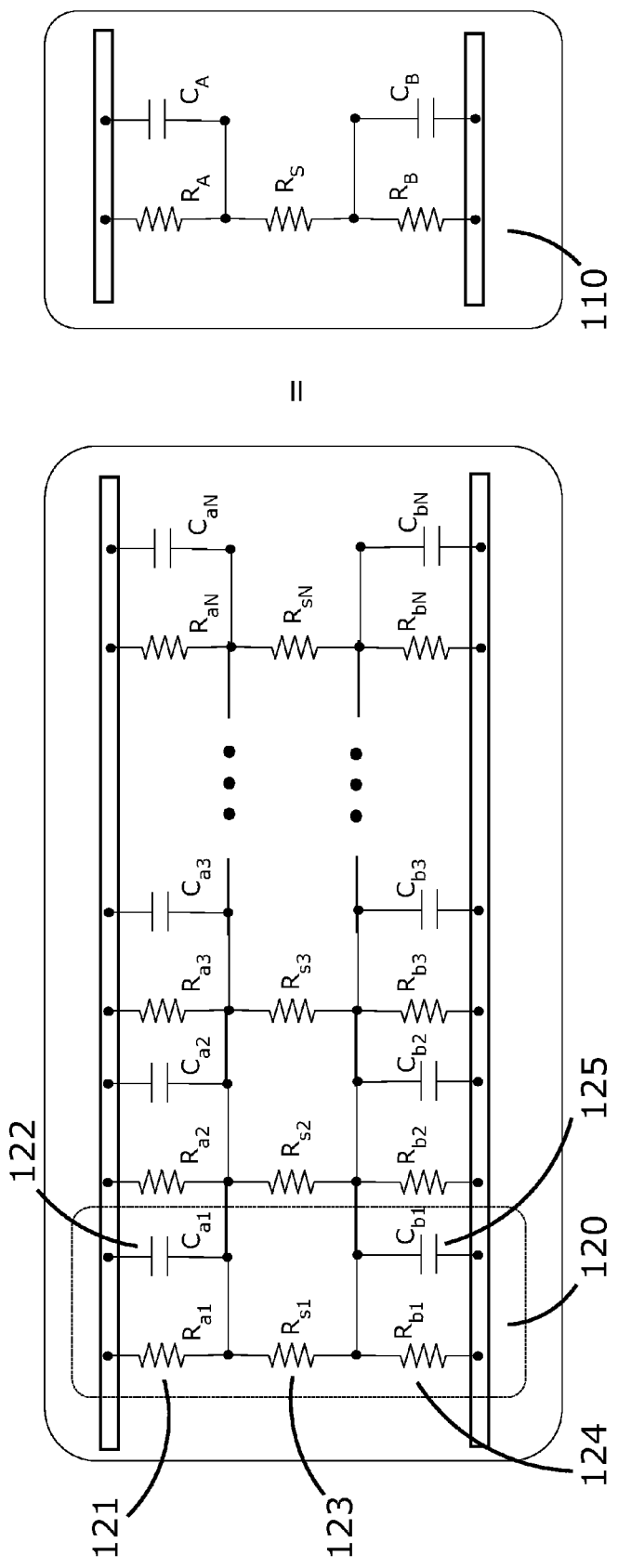
FIG. 4A is a schematic representation of the capacitor matrix array depicting the equivalent circuit.

FIG. 4A shows the equivalent circuit 110 of the VEGF Biosensor 100 and how the circuit can be decomposed to model for each pair of capacitive plates 103 in the capacitor matrix array. Each pair of capacitive plates 103 forms an electrode-electrolyte interface with the solution which can be represented with an equivalent circuit 120. Because the solution medium is dynamic, the circuit for each plate pair is shorted at the electrode/solution interface. Thus, the equivalent circuit of the entire sensor 110 can be written as the combined circuits of each plate pair, which is electrically in parallel to its neighbor pair. Equations 9-13 allow the parameters of 110 be derived from the parameters of each plate pair 120.

$$C_A = C_{a1} \| C_{a2} \| \cdots \| C_{aN} = \sum_N C_{ai} \quad (9)$$

$$C_B = C_{b1} \| C_{b2} \| \cdots \| C_{aN} = \sum_N C_{bi} \quad (10)$$

$$R_A = R_{a1} \| R_{a2} \| \cdots \| R_{aN} = \frac{1}{\sum_N \frac{1}{R_{ai}}} \quad (11)$$

$$R_B = R_{b1} \| R_{b2} \| \cdots \| R_{bN} = \frac{1}{\sum_N \frac{1}{R_{bi}}} \quad (12)$$

$$R_S = R_{s1} \| R_{s2} \| \cdots \| R_{sN} = \frac{1}{\sum_N \frac{1}{R_{ci}}} \quad (13)$$

Figure 5:
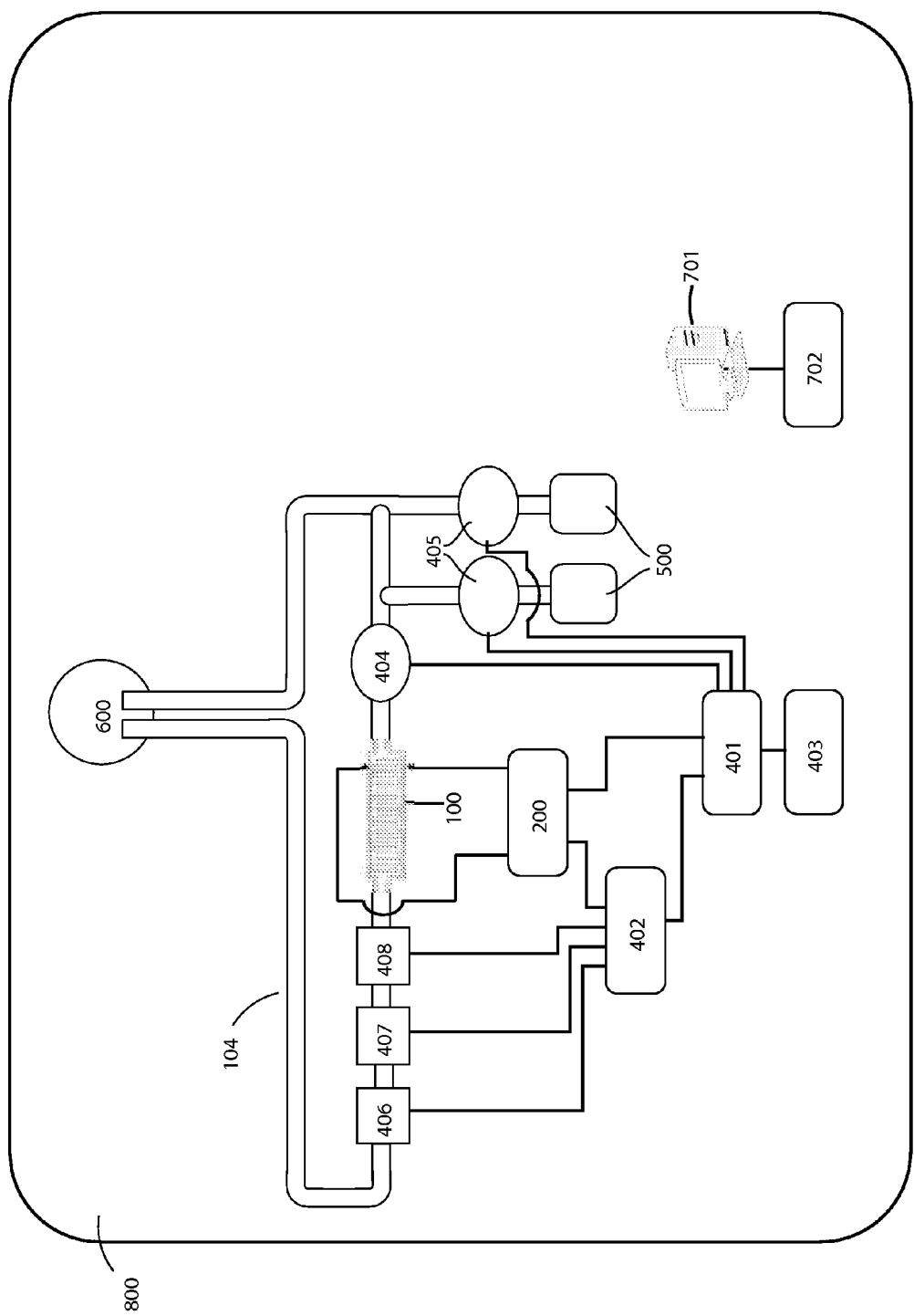
FIG. 5 is an illustrative layout of the VEGF detector configured within a block diagram of the delivery apparatus.

FIG. 5 is the block diagram of a possible layout of the delivery apparatus 800 including the VEGF Biosensor 100. The diagram shows the VEGF Biosensor 100 in series with other physiological sensors including pressure sensor 406, pH sensor 407, and SpO$_2$ 408 along the catheter tubing 104. A piezoelectric pump 404 circulates the cerebrospinal fluid from the tumor site 600 through the series of sensors. The data from the sensors are acquired by a TI-ADS8344 analog to digital converter 402 for processing by the TI-MSP430 microcontroller 401, which controls the delivery of anti-cancer medications from reservoirs 500 via a set of pumps 405. The MICS transceiver allows the implanted delivery apparatus 800 to be in communication with physician computer 701 via the MICS base station 702.

Figure 5A:
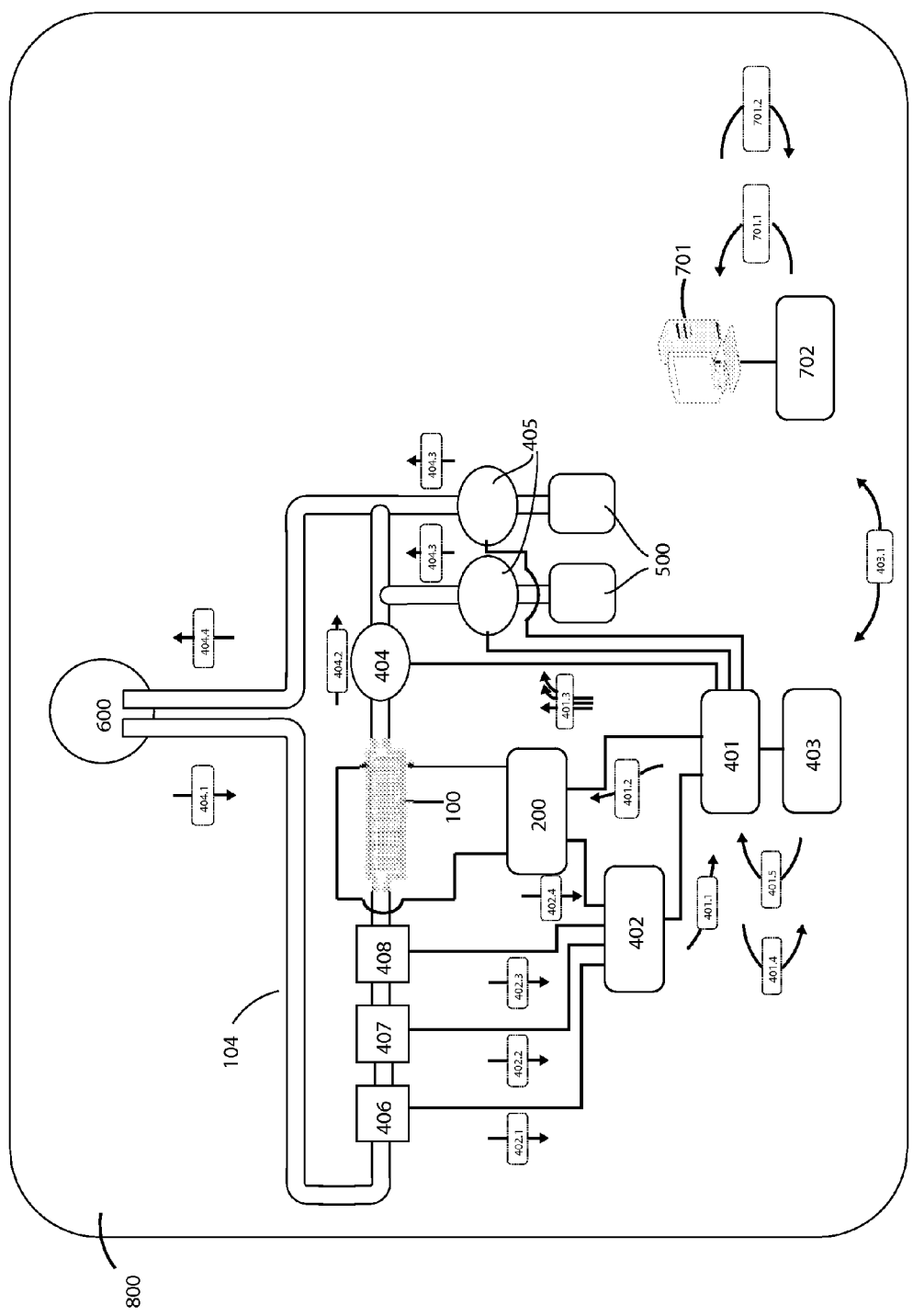
FIG. 5A is a schematic block diagram of the preferred embodiments—biosensor incorporated as part of detecting, analyzing, and reporting system.

FIG. 5A describes the data flow and control mechanism in a possible layout of the delivery apparatus 800 of FIG. 5. The regulation of the amount of VEGF 1, available for vasculogenesis at the tumor site 600, is accomplished by a circulation pump 404, which controls fluid flow 404.2, bringing test samples from tumor site 404.1, and delivering injected anti-cancer medication 404.4. Additional set of pumps 405 regulates injection of anti-cancer medication 404.3, from reservoirs 500. The test samples brought back from the tumor site are circulated through a series of sensors to acquire information regarding the growth of the tumor and progress of anti-cancer medication treatment. The sensors such as pressure sensor 406, pH sensor 407, SpO$_2$ 408, and VEGF biosensor 100 convert physical and biological information into electrical signals 402.1, 402.2, 402.3, and 402.4. The signals are transformed into data numbers 401.1, by the ADC 402 for processing by microcontroller 401. The microcontroller 401 closes the feedback path for the homeostatic loop (described in FIG. 5B) by sending control signals 401.3, to the pumps 404 and 405, leading to the injection of the anti-cancer medication 404.3. The injection regime is programmed in the "Lookup Tables" or models inside the microcontroller and can be updated 401.5, via the Zarlink-70101 medical implant communications services (MICS) transceiver 403. The MICS transceiver is also used to wirelessly transmit 403.1, sensor data and device status to physician computer 701, for real-time monitoring and data logging 701.1.

Figure 5B:
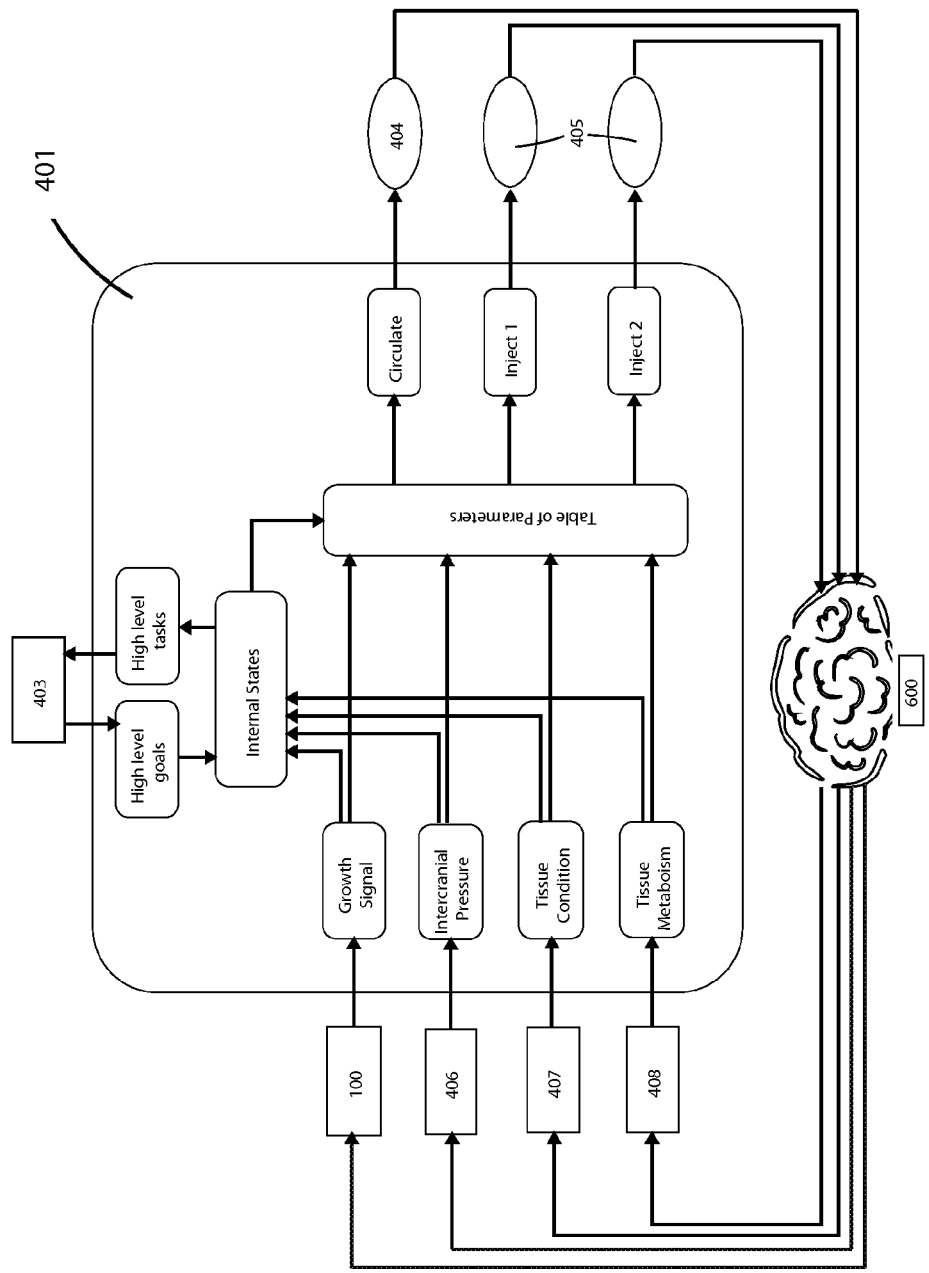
FIG. 5B is a schematic block diagram of the homeostatic loop formed while employing the preferred embodiments of the biosensor.

FIG. 5B is an orthographic representation of the homeostatic loop 801, formed by the embodiments of this invention. The homeostatic approach is used to achieve a stable state of equilibrium that limits the tumor growth while not endangering the surrounding tissues near the tumor site. The homeostatic approach is programmed inside the microcontroller 401 with inputs from sensors such as VEGF biosensor 100, pressure 406, pH 407, and SpO$_2$ 408. Information pertaining to tumor growth such as growth factor, intracranial pressure, tissue condition, and metabolic rate are extracted to determine the progress of treatment based on the parameters in the "lookup table". The sensor information is also used to calculate the internal states which permit adaptation of the system to achieve the desired parameters. The "lookup table" produces actuation parameters to control the pumps that affect the conditions in the tumor site 600. The internal states can be updated based on external inputs from the physician via the wireless transceiver 403.

Table 1, below, shows a collated list of markers associated with different cancers as listed in several reference cancer databases (e.g. U.S. National Cancer Institute, U.K. Cancer Research). These biomarkers found in human serum are known to be reliable for diagnosis and prognosis of the disease. Utilizing the process and method disclosed in this patent would allow a person familiar with the art of biochemistry to produce similar results with various antibodies. So, for example, the specific antibodies to each of the biomarkers presented in Table 1 may be utilized to create a biosensor specific to that biomarker. A person familiar with the art of biosensors would be able to foresee the technologies utilized in this patent to be extended to the construction of biosensors relying on, but not limited to, the cancer markers presented in Table 1.

TABLE 1

| Cancer Type Disease | Biomarker |
|---|---|
| Prostate | Prostate-Specific Antigen (PSA), Prostate Acid Phosphatase (PAP) |
| Breast | Cancer Antigen 15-3 (CA15-3), Cancer Antigen 125 (CA125), Cancer Antigen 27.29 (CA27.29), Carcinoembryonic Antigen breast cancer 1, early onset (CEABRCA1), Breast Cancer Type 2 susceptibility protein (BRCA2), Mucin 1, cell surface associated (MUC-1), Carcinoembryonic Antigen (CEA), ankyrin repeat domain 30A (NY-BR-1), Inhibitor of growth protein 1 (ING-1) |
| Leukemia | Chromosomal abnormalities |
| Testicular | α-Fetoprotein (AFP) β-human chorionic gonadatropin, cancer antigen 1 (CAGE-1), cancer/testis antigen 1B (ESO-1) |
| Ovarian | Cancer Antigen 125 (CA125), Alpha-fetoprotein (AFP), Human chorionic gonadotropin (hCG), |

TABLE 1-continued

| Cancer Type Disease | Biomarker |
|---|---|
| | Tumor protein 53 (p53), |
| | Carcinoembryonic Antigen (CEA) |
| Any solid tumor | Circulating tumor cells in biological fluids, expression of targeted growth factor receptors |
| Colon and pancreatic | Carcinoembryonic Antigen (CEA), Cancer Antigen 19-9 (CA19-9), Cancer Antigen 24-2 (CA24-2), Tumor protein 53 (p53) |
| Lung | Cancer/testis antigen 1B (NY-ESO-1), Carcinoembryonic Antigen (CEA), Cancer Antigen 19-9 (CA19-9), Squamous cell carcinoma (SCC), Cytokeratin fragments (CYFRA21-1), Neuron-specific enolase (NSE) |
| Melanoma | Tyrosinase, Cancer/testis antigen 1B (NY-ESO-1) |
| Liver | Alpha-fetoprotein (AFP), Carcinoembryonic Antigen (CEA) |
| Gastric carcinoma | Cancer Antigen 72-4 (CA72-4), Carcinoembryonic Antigen (CEA), Cancer Antigen 19-9 (CA19-9) |
| Esophagus carcinoma | Squamous cell carcinoma (SCC) |
| Trophoblastic | Squamous cell carcinoma (SCC), Human chorionic gonadotropin (hCG) |
| Bladder | brown adipose tissue (BAT), Fibrin-fibrinogen degradation products (FDP), Nuclear matrix protein 22 (NMP22), Bladder Cancer Antigen 4 (BLCA-4), Cytokeratin fragments (CYFRA 21-1) |

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub combination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

What is claimed is:

1. An anti-VEGF monoclonal half-antibody (a-VEGF mhAb) probe complex for detecting the presence of a target VEGF molecule in a detector, the probe complex comprising:
   an electrode in the detector; and
   a-VEGF mhAb on the electrode capable of binding to indicator VEGF protein and capable of immobilizing the indicator VEGF protein to enable detection of the target VEGF molecule by the detector.

2. The a-VEGF mhAb probe complex of claim 1 where the a-VEGF mhAb enables binding with high specificity to VEGF protein, and further comprising a circuit coupled to the electrode to selectively release the binding to the VEGF protein by application of electric current to the electrode and to thereby allow for re-use of the probe complex.

3. The a-VEGF mhAb probe complex of claim 1 where the a-VEGF mhAb enables binding with high specificity to VEGF protein, and further comprising a fluidic circuit to selectively release the binding by application of fluid flow provided by the fluidic circuit.

4. The a-VEGF mhAb probe complex of claim 2 where the a-VEGF mhAb enables binding with high specificity to VEGF protein, and further comprising a fluidic circuit to selectively release the binding by application of fluid flow provided by the fluidic circuit.

5. The a-VEGF mhAb probe complex of claim 4 in combination with a source of fluid and where the fluidic circuit to selectively release the binding by application of fluid flow provided by the fluidic circuit comprises a piezoelectric pump having an input fluidicly coupled to the source of fluid and an output fluidicly coupled to the electrode, the piezoelectric pump and, electrode being arranged and configured to allow fluidic flushing of the electrode by fluid flow provided by the piezoelectric pump.

6. The a-VEGF mhAb probe complex of claim 1 where the a-VEGF mhAb is composed of chemically split Avastin®.

7. The a-VEGF mhAb probe complex of claim 1 where the a-VEGF mhAb is composed of chemically split humanized monoclonal antibody VEGF (rhuMab VEGF; bevacizumab).

8. The a-VEGF mhAb probe complex of claim 1 where the detector includes a silicon substrate and further comprising a linker composed of a-VEGF mhAB attached to maleimide-terminated self assembled monolayer (m-SAM) bonded to the silicon substrate by silanization with an amine group.

9. A sensor array of a target comprising:
   a substrate;
   a plurality of insulated micro machined capacitors on at least a portion of which the substrate is disposed, the capacitors being arranged in an interdigitated pattern;

a recognition group attached to the plurality of capacitors, the recognition group specifically binding to the target;
a detector circuit for sensing the plurality of capacitors; and
means for reconfiguring the recognition group to allow for reuse of the sensor array.

10. The sensor array of claim 9 where at least one of the plurality of capacitors has a plurality of areas, each of the plurality of areas having a recognition group attached to the area and further comprising a circuit coupled to the plurality of areas to selectively release the binding to the target by application of electric current to the plurality of capacitors and to thereby allow for reuse of the sensor array.

11. The sensor array of claim 9 further comprising a fluidic circuit to selectively release the binding of the recognition group by application of fluid flow provided by the fluidic circuit.

12. The sensor array of claim 11 further comprising a fluidic circuit to selectively release the binding of the recognition group by application of fluid flow provided by the fluidic circuit.

13. The sensor array of claim 12 in combination with a source of fluid and where the fluidic circuit utilized to selectively release the binding of the recognition group by application of fluid flow provided by the fluidic circuit comprises a piezoelectric pump having an input fluidicly coupled to the source of fluid and an output fluidicly coupled to the plurality of capacitors, the piezoelectric pump and the plurality of capacitors being arranged and configured to allow fluidic flushing of the electrode by fluid flow provided by the piezoelectric pump.

14. The sensor array of claim 9 where the recognition group is composed of chemically split Avastin®.

15. The sensor array of claim 9 where the recognition group is composed of chemically split humanized monoclonal antibody VEGF (rhuMab VEGF; bevacizumab).

16. The sensor array of claim 9 where the recognition group comprises a-VEGF mhAb capable of binding to indicator VEGF protein and capable of immobilizing the indicator VEGF protein on the capacitors to enable detection of the target VEGF molecule by the detector.

17. The sensor array of claim 9 further comprising a microcontroller coupled to the sensor array and where at least one of the plurality of capacitors has a recognition group that binds to the target and the detector detects presence of the target on at least one of the capacitors and communicates detection of the target to the microcontroller.

18. The sensor array of claim 16 further comprises a linker disposed on at least a portion of at least one capacitor to immobilize a-VEGF mhAb on the at least one capacitor.

19. The sensor array of claim 18 where the linker comprises Succinimidyl-4-(N-maleimidomethyl)cyclohexane-1-carboxylate, and a hybridization substance (3-aminopropyl-trimethoxysilane).

20. A system for detecting a target of a-VEGF mhAb in a fluid comprising:
a sensor comprising:
a substrate;
a sealed micromachined mesh capacitor array on at least a portion of which the substrate is disposed;
a recognition group attached to the substrate, the recognition group selectively binding to the target of a-VEGF mhAb; and
a detector for detecting binding of the target of a-VEGF mhAb by the recognition group;
a delivery system for delivering the fluid for analysis to the sensor; and
means for reconfiguring the recognition group to allow for selective release of the target to allow reuse of the sensor array.

21. The system of claim 20 where the delivery system includes an input port, a reservoir for the fluid connected to the input port, and an output port connected to the reservoir, at least a portion of the substrate being exposed to the fluid in the reservoir.

22. The system of claim 20 where the capacitor array has a predetermined capacitance selected to enable target binding of a maximum amount of functionalized surface area of the capacitor array, and where the delivery system is dimensionally and structurally arranged and configured as a function of the predetermined capacitance to provide unrestricted flow of the fluid through the sensor.

23. The system of claim 20 where the means for reconfiguring the recognition group to allow for selective release of the target to allow reuse of the sensor array comprises a circuit coupled to the plurality of areas to selectively release the binding to the target by application of electric current to the capacitor array and to thereby allow for reuse of the sensor array, or a fluidic circuit to selectively release the binding by application of fluid flow provided by the fluidic circuit.

24. A method of real-time in vivo detection of VEGF in patient fluid comprising:
chemically splitting humanized monoclonal antibody VEGF (rhuMab VEGF; bevacizumab);
attaching the split humanized monoclonal antibody VEGF to capacitor surfaces in a sensor;
exposing the sensor to a fluid including VEGF to be analyzed using the split humanized monoclonal antibody VEGF;
binding the VEGF to the measurement surfaces within the sensor by binding the VEGF to the split humanized monoclonal antibody VEGF to form a ligand hybridized target VEGF as an analyte molecule; and
detecting the analyte molecule to measure the hybridized target VEGF; and
generating an output from the sensor indicative of the measured hybridized target VEGF.

25. The method of claim 24 where chemically splitting humanized monoclonal antibody VEGF (rhuMab VEGF; bevacizumab) comprises chemically splitting Avastin®.

26. The method of claim 24 where detecting the analyte molecule comprises detecting a change in a capacitive value of the sensor through changes in a magnitude of sensor impedance, or time rate of change of sensor impedance.

27. The method of claim 24 where chemically splitting humanized monoclonal antibody VEGF (rhuMab VEGF; bevacizumab) comprises splitting an anti-VEGF monoclonal antibody (a-VEGF mAb) into two half-antibodies by using tris (2-carboxyethyl) phosphine (TCEP) as reduction agent to selectively cleave disulfide bonds that connect the two heavy chains of a mAB to produce two anti-VEGF half-antibodies (mhAb).

28. The method of claim 24 further comprising providing guided therapeutic intervention of at least one medicating agent dependent on the real-time in vivo detection of VEGF in patient fluid.

* * * * *